United States Patent [19]

Nuell et al.

[11] Patent Number: 5,658,792
[45] Date of Patent: Aug. 19, 1997

[54] ANTIPROLIFERATIVE PROTEIN

[75] Inventors: Mark J. Nuell, Ellicott City, Md.; J. Keith McClung, Ardmore, Okla.; David A. Stewart, Baltimore; David B. Danner, Columbia, both of Md.

[73] Assignee: The United States of America as represented by the Department of Health and Human Services, Washington, D.C.

[21] Appl. No.: 612,674

[22] Filed: Nov. 14, 1990

[51] Int. Cl.[6] .......................... C12N 15/12; C12N 15/63; C12N 1/21; C07K 14/47
[52] U.S. Cl. ..................... 435/252.33; 536/23.5; 536/24.31; 435/69.1; 435/71.2; 435/252.3; 435/172.3; 435/320.1; 935/11; 935/29; 935/56; 935/72; 935/73
[58] Field of Search .................. 435/69.1, 71.2, 435/252.3, 252.33, 172.3, 320.1; 536/27, 23.5; 935/11, 29, 56, 72, 73

[56] References Cited

PUBLICATIONS

P.D. Eveleth et al. "Sequence and Expression of the Cc Gene . . ." Nuc. Acids. Res. 14(15)6169–6183 (1986).
M.J. Nuell et al. "Molecular and Genetic Analysis of Prohibitin . . . " J. Cell. Biochem. 14C:307 Abst. #1418 (Feb. 1990).
McClung, J.K. et al. "Isolation of a cDNA that Hybrid Selects Antiproliferative mRNA from Rat Liver." Biochem., Biophys. Res. Commun. 164(3)1316–1322 (Nov. 1989).

*Primary Examiner*—Robert A. Wax
*Assistant Examiner*—Rebecca Prouty
*Attorney, Agent, or Firm*—Birch, Stewart, Kolasch & Birch, LLP

[57] ABSTRACT

The subject invention relates to a novel mammalian antiproliferative protein, prohibitin, and uses thereof. For example, prohibitin may be utilized in the treatment of diseases involving excess cellular replication, such as cancer, or in the treatment of conditions involving an insufficient amount of cellular replication, such as impaired tissue regeneration.

18 Claims, 20 Drawing Sheets

```
  1  GAAGGAGTC ATG GCT GCC AAA GTG TTT GAG TCC ATC GGA AAG TTC GGC CTG
             MET Ala Ala Lys Val Phe Glu Ser Ile Gly Lys Phe Gly Leu

52  GCC TTA GCA GTT GCA GGA GGC GTG GTG AAC TCT GCT CTA TAT AAC GTG
     Ala Leu Ala Val Ala Gly Gly Val Val Asn Ser Ala Leu Tyr Asn Val

100  GAT GCC GGA CAC AGA GCT GTC ATC TTC GAC CGA TTC GGC GTG CAG
     Asp Ala Gly His Arg Ala Val Ile Phe Asp Arg Phe Arg Gly Val Gln

148  GAC ATC GTG GTA GGG GAA ACT CAC GGG ACT CTC ATC CCC TGG GTA CAG
     Asp Ile Val Val Gly Glu Gly Thr His Gly Thr Leu Ile Pro Trp Val Gln

196  AAG CCA ATC ATC TTT GAC TGC CGC TCT CGA AAT GTG CCG GTC
     Lys Pro Ile Ile Phe Asp Cys Arg Ser Arg Asn Val Pro Val

244  ATC ACC GGC AGC AAA GAC TTG CAG CTT CAG AAT GTC AAC ATC CTA CGT ATC
     Ile Thr Gly Ser Lys Asp Leu Gln Asn Val Asn Ile Thr Leu Arg Ile

292  CTC TTC CGG CCG GTG GCC AGC CAG CTT CCT CGT TAC ATC CGT AGC ATT
     Leu Phe Arg Pro Val Ala Ser Gln Leu Pro Arg Ile Tyr Thr Ser Ile

340  GGC GAG GAC TAT GAT GAG CGG GTG CTG CCA TCT ATC ACC ACA GAG ATC
     Gly Glu Asp Tyr Asp Glu Arg Val Leu Pro Ser Ile Thr Thr Glu Ile
```

FIG. 3A

```
388  CTC AAG TCG GTG GTG GCT CGA TTC GAT GCT GGA GAA TTG ATT ACC CAG
     Leu Lys Ser Val Val Ala Arg Phe Asp Ala Gly Glu Leu Ile Thr Gln

436  CGA GAG CTG GTC TCC AGG CAG GTG AGT GAT GAC CTC ACA GAG GAG CGA GCA
     Arg Glu Leu Val Ser Arg Gln Val Ser Asp Asp Leu Thr Glu Arg Ala

484  GCA ACA TTC GGG CTC ATC CTG GAT GTG TCC CTG ACA CAT CTG ACC
     Ala Thr Phe Gly Leu Ile Leu Asp Asp Val Ser Leu Thr His Leu Thr

532  TTC GGG AAG GAG TTC ACA GAG GCG GTG GAA CTC AAA CAG GTG GCT CAG
     Phe Gly Lys Glu Phe Thr Glu Ala Val Glu Lys Gln Val Ala Gln

580  CAG GAA GCA GAG AGA GCC TTT GTG GAA AAG GCT GAG CAG CAG
     Gln Glu Ala Glu Arg Ala Phe Val Glu Lys Ala Glu Gln Gln

628  AAG GCG GCC ATC ATC TCT GCT GAG GGT GAC TCC AAA GCG GCT GAG
     Lys Ala Ala Ile Ile Ser Ala Glu Gly Asp Ser Lys Ala Ala Glu

676  CTG ATC GCC AAC TCA CTG GCC ACC GCC GGG GAT GGC CTG ATC GAG CTG
     Leu Ile Ala Asn Ser Leu Ala Thr Ala Gly Asp Gly Leu Ile Glu Leu

724  CGA AAG CTG GAA GCT GCT GAG GAC ATT GCT TAT CAG CTC TCC CGC TCT
     Arg Lys Leu Glu Ala Ala Glu Asp Ile Ala Tyr Gln Leu Ser Arg Ser
```

FIG. 3B

```
772   CGG AAC ATC ACC TAC CTG CCA GCA GGG CAG TCC GTG CTC CTC CAG CTC
      Arg Asn Ile Thr Tyr Leu Pro Ala Gly Gln Ser Val Leu Leu Gln Leu

820   CCC CAG TAA GGCCAGCCAG CCAGGGCCTC CATCGCTCTG AATGACGCCT
      Pro Gln *

869   TCCTTCTGCC CCACCCCAGA AATCACTGTG AA ATTTA ATG ATTGGCTTAA CATGAAGGA A

929   ATAA AGGTAA AATCACTTCA TATCTCTAAT TATCAAATGA AGCTTTTATT GTTACACTTT

989   TTGCCCACTT TCATAACAAA ATTGCCAAGT GCCTATGCAG ACTGGCCTTC CACCCTGGGT

1049  GCTGGCAGTC GGCGGAAGAA AGGCAGGGCA GTGTGTGTGG TGGACGGGGA GCCAGCTGGC

1109  AGCCTGAGTA GACCTTGAGC CTCCATTCTG AAGCCCTCAA TTTTTCCAGC CCATATATTG AAG ATTTA CA GACAGTGGTG

1169  CACACACGTG AACCAAAAGC AAGCCCTCAA AAGTGGTCTG TCTTAACTGT CATACGAACC CGGACAGATG

1229  CAGCTGAGGA GGGCCTGAGG AAGTGGTCTG TGTGCGTGCG AAGGCCATTC CCTCTTAACC

1289  GTGACCAGCG GAAGCAGGTG TGTGCGTGCG ACTAGGGCAT GGAGTGAAGA ATCTGCCCAT

1349  CACGGTGGGT GGGCCTAATT TTGCTGCCCC CACCAGAGAC CTAAACTTTG GATAGACTTG
```

FIG. 3C

```
1409  GATAGAATAA GAGGCCTGGA CTGAGATGTG AGTCCTGTGG AAGACTTCCT GTCCACCCCC
1469  CACATTGGTC CTCTCAAATA CCAATGGGAT TCCAGCTTGA AGGATTGCAT CTGCCGGGGC
1529  TGAGCACACC TGCCAAGGAC ACGTGCGCCT GCCTTCCCGC TCCCTCTCTT CGAGATTGCC
1589  CTTCCTTCCC AAGGGCTGTG GGCCAGAGCT CCGAAGGAAG CAATCAAGGA AAGAAAACAC
1649  AATGTAAGCT GCTGTC AATA AA TGACACCC AGACCCTC (AAA) n
```

FIG. 3D

```
 12  ATGGCTGCCAAAGTGTTTGAGTCCATCGGAAAGTTCGGCCTGGCCTTAGC
     |||||||  |   |   |||   |||| ||  ||| |||   |   |
 27  ATGGCTGCTCAGTTCTTTAATCGCATTGGCCAAATGGGCTCGGAGT••GG

62  AGTTGCAGGAGGCGTGGTGAACTCTGCTCTATATAACGTGGATGCCGGAC
     |||      || ||||||| ||  ||  || ||  |||||||| ||||| |
 75  CGTTTTGGGTGGCGTTGTCAATTCGGCATTATATAATGTGGAAGGCGGCC

112  ACAGAGCTGTCATCTTCGACCGATTCCGTGGCGTGCAGGACATCGTGGTA
     || | || |||||||||||| || |||    ||| |  |||| |||||||
125  ACCGGGCGGTCATCTTCGATCGCTTCACCGGCATCAAGGAGAACGTGGTC

162  GGGGAAGGGACTCACTTCCTCATCCCCTGGGTACAGAAGCCAATCATCTT
     || || || || || |||||||| |||||||| ||| |||   ||||||||
175  GGCGAGGGTACCCACTTCTTCATCCCATGGGTGCAGCGGCCCATCATCTT

212  TG••ACTGCCGCTCTCGACCACGTAATGTGCCGGTCATCACCGGCAGCAA
      |   |   ||| || |  || || || || || |  || || ||||||||
225  CGGACCATCCGGTCCCAGCCCCGCAACGTTCCAGAGATAACGGGCAGCAA

260  AGACTTGCAGAATGTCAACATCACACTACGTATCCTCTTCCGGCCGGTGG
     ||  |||||||||||||||||||| ||  || ||  |  |||   ||  |
275  GGATCTGCAGAATGTCAACATCACGCTCCGAATCCTGTACCGCCCCATTC

310  CCAGCCAGCTTCCTCGTATCTACACCAGCATTGGCGAGGACTATGATGAG
     |   |||||| ||  |||||||||||   | ||| |||||||| || |||
325  CAGACCAGCTGCCCAAGATCTACACCATTCTCGGCCAGGACTACGACGAG

360  CGGGTGCTGCCATCTATCACCACAGAGATCCTCAAGTCGGTGGTGGCTCG
     || ||  || ||||| |  |   ||    | |||||
375  CGTGTCCTGCCCTCCATCGCGCCTGAGATG••••••••••••••••••••

410  ATTCGATGCTGGAGAATTGATTACCCAGCGAGAGCTGGTCTCCAGGCAGG
                                       || || ||  |
405  •••••••••••••••••••••••••••••••••••GTGTCGCAGCGCG

460  TGAGTGATGACCTCACAGAGCGAGCAGCAACATTCGGGCTCATCCTGGAT
     |     |  || || || | | ||  | | |||||| | || |||||||
418  TTTCCCAGGAACTGACTGTACGTGCCAAGCAGTTCGGCTTTATTCTGGAT

510  GACGTGTCCCTGACACATCTGACCTTCGGGAAGGAGTTCACAGAGGCGGT
     ||| | |  ||  || || ||||||||| |  |||||||||| |||  ||
468  GACATCTCGCTCACGCACTTGACCTTCGGTCGGGAGTTCACGCTGGCCGT

560  GGAAGCCAAACAGGTGGCTCAGCAGGAAGCAGAGAGAGCCAGATTTGTGG
     | ||   |  ||||||| ||||||||  |||||||  ||| | ||||| |
518  CGAGATGAAGCAGGTGGCCCAGCAGGAGGCGGAGAAGGCGCGTTTTGTCG

610  TGGAAAAGGCTGAGCAGCAGAAGAAGGCGGCCATCATCTCTGCTGAGGGT
     ||||   ||| |||||||| ||| |||||||| | |  |  || ||||||
568  TGGAGAAGGCCGAGCAACAGAAGCTGGCGTCCATTATTTCGGCGGAGGGT

660  GACTCC•AAAGCGGCTGAGCTGATCGCCAACTCACTGGCCACCGCCGGGG
     ||   |  ||||||||||| ||||| ||||| ||||| |    |||||||
618  GATGCCGAACGCGCCTG•••TGTTGGCCAAGTCATTG••CGAGGCCGGAG
```

FIG. 6A

```
709  ATGGCCTGATCGAG•CTGCGAAAGCTGGAAGCTGCTGAGGACATTGCTTA
     | || ||| | ||| |||||| | | | | || |||     || |
663  ACGGTCTGGTGGAGCCTGCGACTGATTG•ACCGGCCGAGATATCGCCTCA

758  TCAGCTCT•CCCGCTCTCGGAACATCACCTACCTGCCAGCAGGGCAGTCC
     ||||| | |||| || ||       || |||||| ||||   || ||| |
712  CCAGCTATCCCCGGTCCCGTGGAGTCGCCTACTTGCCCAGCGGACAGAGC

807  •GTGCTCCTCCAGCTCCC
      ||| ||| | || ||
762  CACGCTGCTCAATCTGCC
```

```
                        0                                      50
DM4 AA          METAlaAlaGlnPhePheAsnArgIleGlyGlnMETGlyLeuGlyValAlaVal
DM4 N   aacaagcaagataaatggctgctcagttctcttaatcgcattggccaaatgggcctcggagtggccgtt
Cc  N   AACAAGCAAGATAAATGGCTGCTCAGTTCTCTTAATCGCATTGGCCAAATGGGC TCGGAGTGGC GTT
Cc  AA          METAlaAlaGlnPhePheAsnArgIleGlyGlnMETGly SerGluTrpA rgP
                                                                        ↑
LeuGlyGlyValValAlaAsnSerAlaLeuTyrAsnValGlyLeuGlyHisArgAlaValIlePheAspArgPheThrG
ttgggtgggcggttgtcattcggcattatataatgtggaaggggccacggggtcatcttcgatcgcttcaccg
TTGGGTGGCGGTTGTCAATTCGGCATTATATATAATGTGGAAGGCGGCCACCGGGTCGGTCATCATCGATCGCTTCACCG
heGlyTrpArgCysGlnPheGlyIleIle* METTrpLysAlaThrGlyArgSerSerIleAlaSerPro
                                                     100                    ↑
                                                                       200
lyIleLeuLysGluAsnValValGlyGluGlyThrHisPhePheIleProTrpValGlnArgProIleIlePhe Asp
gcatcaaggagaacgtggtcggcgagggtacccactctcttcatcccatggtgcagcggcccatcatcttc gac
GCATCAAGGAGAACGTGGTCGGCGAGGGTACCCACTTCTTCATCCCATGGTGCAGCGGCCCATCATCTTCGGACC
AlaSerArgArgThrTrpSerAlaArgValProThrSerSer*METGlyAlaAlaAlaHisHisLeuArgThr
                                                                            ↑
IleArgSerGlnProArgAsnValProValIleThrGlySerLysAspLeuThrIleLeuGlyGlnAsnValAsnIleThrLeuArgI
atccgtcccagccccgcaacgttcctgtgataacgggcagcaaggatctgcagaatgtcaacatcacgctccgaa
ATCCGGTCCCAGCCCCGCAACGTTCCAGAGATAACGGGCAGCAAGGATCTGCAGAATGTCAACATCACGCTCCGAA
IleArgSerGlnProArgAsnValProValIleThrGlySerLysAspLeuThrIleLeuGlyGlnAsnValAsnIleThrLeuArgI
                                                       350
                                                                 300
leLeuTyrArgProIleProAspGlnLeuProLysIleTyrThrIleLeuGlyGlnAspTyrArgLeuArgVal Le
tcctgtaccgcccattccagaccagctgcccaagatctacaccattctcggccaggactaccggctgcgtgtcct
TCCTGTACCGCCCATTCCAGACCAGCTGCCCAAGATCTACACCATTCTCGGCCAGGACTACCGGCTGCGTGTCCT
leLeuTyrArgProIleProAspGlnLeuProLysIleTyrThrIleLeuGlyGlnAspTyrArgLeuArgValLe
```

```
                                          650
sAlaArgPheValValGluLysAlaGluLysLeuAlaSerIleIleSerAlaGluGlyLysAspAlaGluAla
ggcgcgtttgtcgtggagaaggccgagcaacagaagctggcgtccatcattcggcggagggtgatgccgaagcc
GGCGCGTTTGTCGTGGAGAAGGCCGAGCAACAGAAGCTGGCGTCCATTATTCGGCGGAGGGTGATGCCGAAGCC
sAlaArgPheValValGluLysAlaGluLysLeuAlaSerIleIleSerAlaGluGlyLysAspAlaGluArg
                                                                        ←
                      700
Al aGlyLeuLeuAlaLysSerLeuAlaGluAlaGlyLysAspGlyLeuValGluL euArgArgIleGluAlaA laG
gc tggcctgttggccaagtcattcggcggagccggagacggtctggtgagc tgcgacgtattgaggccg ccg
GCCTG    TGTTGGCCAAGTCATTCGC   GAGGCCGGAGACGGTCTGGTGGAGAGCCTGCGACCTGACTGA   CCGGCCG
AlaCy    sValGlyGlnValIleIleAl   aArgProGluThrValTrpTrpSerLeuArgLeuIleAs  pArgPro
   ↑750 ↑ ↑                                                ↑ 800 ↑ ↑       ↑    ↑
luAspIleAlaT yrGlnLeuSerA rgSerArgGlyValAlaAlaTyrLeuProSerGlyGlnSer ThrLeuLeuAs
aggatatcgcct accagctatccc ggtcccgtggtgtgcctactgcccagcggacagagc acgctgctcaa
AG ATATCGCCTCACCAGCTATCCCCGGTCCCGTGGTGTGCCTACTTGCCCAGCGGACAGAGCCACGCTGCTCAA
Ar gTyrArgLeuThrSerTyrProArgSerArgGlyValAlaAlaTyrLeuProSerGlyGlnSerHisAlaAlaGln
                                    ↑ 850        ↑
nLeuProSerThrIleAlaGlnTER
tctgccatcgaccatcgcgcagtagctgggtgcatctagttccgttaagttgtaactacctatagcattt actaa
TCTGCCATCGACCATCGCGCAGTAGCTGGGTGCATCTAGTTCCGTTAAGTTGTAACTACCTATAGCATTTCACTAA
SerAlaIleAspHisArgAlaValAlaAlaGlyCysIleTER
                      900                                        950
gtactttt cgattttgtttctgctgaaatatgcactactctaaagagttcgcgccgactgactggagaatactaa
GTACTTTTCGATTTTGTTTCTGCTGAAATATGCACTACTCTAAAGAGTTCGCGCCGACTGACTGGAGAATACTAA
                     1000                                                  ↑
gcgaaacaaccaaaaatttgtctcatgtaa tcggttttttccattatctttcccgatcgggttcgaaatccggtcgca
GCGAAACAACCAAAAATTTGTCTCATGTAAATCGGTTTTTCCATTATCTTTCCCGATCGG TTCGAAATCCGGTCGCA
                                              ↑
```

```
R                                                                                       Tyr Asp Glu Arg Val Leu Pro Ser Ile Thr
                                                                                        TAT GAT GAG CGG GTG CTG CCA TCT ATC ACC   378
D                                                                                       TAC GAC GAG CGT GTC CTG CCC TCC ATC GCG
                                                                                        Tyr Asp Glu Arg Val Leu Pro Ser Ile Ala   378
Y                                                                                       TAC GAC GAG CGG GTG TTA CCA TCT ATC GGC
                                                                                        Tyr Asp Glu Arg Val Leu Pro Ser Ile Gly

Thr Glu Ile Leu Lys Ser Val Val Ala Arg Phe Asp Ala Gly
R 379   ACA GAG ATC CTC AAG TCG GTG GCT CGA TTC GAT GCT GGA             420
D 379   CCT GAG GTG CTG AAG GCT GTG GTC GCC CAG TTC GAC GCC GGC
        Pro Glu Val Leu Lys Ala Val Val Ala Gln Phe Asp Ala Gly         420
Y       AAT GAG GTT TTA AAG TCT ATA GTA GCT CAA TTT GAT GCT GCT
        Asn Glu Val Leu Lys Ser Ile Val Ala Gln Phe Asp Ala Ala

Glu Leu Ile Thr Gln Arg Glu Leu Val Ser Arg Gln Val Ser
R 421   GAA TTG ATT ACC CAG CGA GAG CTG GTC TCC AGG CAG GTG AGT         462
D 421   GAG CTG ATC ACC CAG CGT GAG ATG GTG TCG CAG CGC GTT TCC
        Glu Leu Ile Thr Gln Arg Glu MET Val Ser Gln Arg Val Ser         462
Y       GAG TTA ATT ACA CAG AGA GAA ATT ATT TCT CAA AAA ATC AGA
        Glu Leu Ile Thr Gln Arg Glu Ile Ile Ser Gln Lys Ile Arg
```

FIG. 9D

```
R 463  Asp Asp Leu Thr Glu Arg Ala Ala Thr Phe Gly Leu Ile Leu
D 463  GAT GAC CTC ACA GAG CGA GCA ACA TTC GGG CTC ATC CTG   504
       --- --- --- --- --- --- --- --- --- --- --- --- --- ---
       CAG GAA CTG ACT GTA CGT GCC CAG TTC GGC TTT ATT CTG   504
Y      Gln Glu Leu Thr Val Arg Ala Gln Phe Gly Phe Ile Leu

AAA GAG CTT TCT ACG AGG GCC GAA TTC GGT ATT AAG TTG
       Lys Glu Leu Ser Thr Arg Ala Asn Glu Phe Gly Ile Lys Leu

R 505  Asp Asp Val Ser Leu Thr His Leu Thr Phe Gly Lys Glu Phe
D 505  GAT GAC GTG TCC CTG ACA CAT CTG ACC TTC GGG AAG GAG TTC   546
       --- --- --- --- --- --- --- --- --- --- --- --- --- ---
       GAT GAC ATC TCG CTC ACG CAC TTG ACC TTC GGT CGG GAG TTC   546
       Asp Asp Ile Ser Leu Thr His Leu Thr Phe Gly Arg Glu Phe

Y      GAA GAT GTC TCT ATC ACT CAT ATG ACG TTT GGT CCC GAA TTC
       Glu Asp Val Ser Ile Thr His MET Thr Phe Gly Pro Glu Phe
```

FIG. 9E

| | | | | | | | | | | | | | | |
|---|---|---|---|---|---|---|---|---|---|---|---|---|---|---|
| R 547 | Thr<br>ACA | Glu<br>GAG | Ala<br>GCG | Val<br>GTG | Glu<br>GAA | Ala<br>GCC | Lys<br>AAA | Gln<br>CAG | Val<br>GTG | Ala<br>GCT | Gln<br>CAG | Gln<br>CAG | Glu<br>GAA | Ala<br>GCA | 588 |
| D 547 | ACG | GAG | GCC | GTC | GAG | ATG | AAG | CAG | GTG | GCC | CAG | CAG | GAG | GCG | 588 |
| | Thr | Glu | Ala | Val | Glu | MET | Lys | Gln | Val | Ala | Gln | Gln | Glu | Ala | |
| Y | ACG<br>Thr | AAA<br>Lys | GCA<br>Ala | GTT<br>Val | GAG<br>Glu | CAG<br>Gln | ATT<br>Ile | AAG<br>Lys | CAG<br>Gln | GCA<br>Ala | CAG<br>Gln | CAA<br>Gln | GAT<br>Asp | GCC<br>Ala | |
| R 589 | Glu<br>GAG | Arg<br>AGA | Ala<br>GCC | Arg<br>AGA | Phe<br>TTT | Val<br>GTG | Val<br>GTG | Glu<br>GAA | Lys<br>AAG | Ala<br>GCT | Glu<br>GAG | Gln<br>CAG | Gln<br>CAA | Gln<br>CAG | 630 |
| D 589 | GAG<br>Glu | AAG<br>Lys | GCG<br>Ala | CGT<br>Arg | TTT<br>Phe | GTC<br>Val | GTG<br>Val | GAG<br>Glu | AAG<br>Lys | GCC<br>Ala | GAG<br>Glu | CAA<br>Gln | CAG<br>Gln | CAG<br>Gln | 630 |
| Y | GAA<br>Glu | AGA<br>Arg | GCC<br>Ala | AAA<br>Lys | TTC<br>Phe | CTT<br>Leu | GTC<br>Val | GAA<br>Glu | AAG<br>Lys | GCG<br>Ala | GAG<br>Glu | CAA<br>Gln | CAG<br>Gln | CAG<br>Gln | |

FIG. 9F

ANTIPROLIFERATIVE PROTEIN

BACKGROUND OF THE INVENTION

1. Technical Field

The subject invention relates to a novel mammalian antiproliferative protein, prohibitin, and uses thereof. For example, prohibitin may be utilized in the treatment of diseases involving excess cellular replication, such as cancer, or in the treatment of conditions involving an insufficient amount of cellular replication, such as impaired tissue regeneration.

2. Background Information

The ability to negatively regulate cell proliferation is a necessity for all living organisms. Unicellular organisms must limit their replication to the time when adequate nutrients and other environmental factors are present, and multicellular organisms must accurately shape and maintain the architecture of their component tissues. The failure in a multicellular organism to provide adequate negative growth control in the developmental period may result in a malformation, which may be lethal. In the postdevelopmental period, such a failure may result in neoplasia. Because negative control is so critical, specific genes have evolved whose role is actively antiproliferative.

Tumor suppressor genes are a class of genes that have been identified based on an association between neoplasia and the loss of function in both copies of the gene (Klein, G., *Science* 238:1539–45 (1987); Hansen et al., *Cell* 53:172–73 (1988); Ponder, B., *Nature* 335:400–02 (1988); Sager, R., *Science* 246:1406–12 (1989)). While the existence of more than ten tumor suppressor genes is predicted based on such associations, only four such genes have been cloned to date: (1) retinoblastoma (Friend et al., *Nature* 323:643–46 (1986); Lee et al., *Nature* 329:642–45 (1987); Fung et al., *Science* 236:1657–61 (1987)), (2) p53 (Oren et al., *Proc. Natl. Acad. Sci. USA* 80:56–59 (1983)), (3) Wilms' tumors (Call et al., *Cell* 60:509–20 (1990); Rose et al., *Cell* 60:495–508 (1990); Gessler et al., *Nature* 343:774–78 (1990)) and (4) dcc (Fearon et al., *Science* 247:49–56 (1990). The retinoblastoma gene product and p53 appear to be nuclear proteins (Lee et al., *Science* 235:1394–99 (1987); Rotter et al., *J. Virol.* 36:547–55 (1980); Dippold et al., *Proc. Natl. Acad. Sci. USA* 3:1695–99 (1981)). The Wilms' tumor gene product has a structure similar to that of other transcription factors (Call et al., supra; Gessler et al., supra). The dcc gene product resembles neural cell adhesion molecules (Fearon et al., supra).

Tumor suppressor genes may be only a subset of the important negative regulatory genes in the cell. A hypothetical second class of negative regulators would be antiproliferative genes whose loss of function kills the cell. A lethal outcome might occur for any number of reasons, such as when internal growth signals become too great for the maintenance of homeostasis.

In general, negative growth control genes that act within mammalian cells have been extremely difficult to isolate. Despite intensive research in recent years, only a small number of genes have been cloned for whom such an activity is likely. Of this subset, only four genes have been shown to be directly antiproliferative by expressing them in cells in tissue culture: the retinoblastoma gene product (Huang et al., *Science* 242:1563–66 (1988)), p53 (Mercer et al., *Proc. Nat'l Acad. Sci. USA* 87:6166–70 (1990), a ras-related transformation suppressor gene (Kitayama et al., *Cell* 56:77–84 (1989), and prohibitin (McClung et al., *Biochem. Biophys. Res. Commun.* 164:1316–22 (Nov. 15, 1989)).

The first cDNA for prohibitin was isolated using a different strategy than that used to isolate tumor suppressor genes (McClung et al., Supra). This cDNA was originally identified as one of a set of cDNAs corresponding to mRNAs more highly expressed in normal than in regenerating liver. It was then shown that prohibitin mRNA, enriched by hybrid selection, could block DNA synthesis when microinjected into normal fibroblasts. No match was found between the partial cDNA clone and sequences in the GenBank database.

All U.S. patents and publications referred to herein are hereby incorporated by reference.

SUMMARY OF THE INVENTION

The subject invention relates to a novel mammalian antiproliferative protein, prohibitin, and uses thereof.

Complementary DNA for prohibitin has been cloned and analyzed. Moreover, prohibitin messenger RNA has been shown to block DNA synthesis in some cancer cells. Thus, prohibitin or the gene encoding this protein may be useful in the treatment of some diseases or conditions involving cellular multiplication, for example, cancer.

More specifically, the present invention relates to a DNA fragment having the nucleotide sequence as defined in FIG. 3. This fragment may also have a nucleotide sequence that is an allelic or species variation of the sequence defined in FIG. 3. The fragment encodes the antiproliferative protein prohibitin.

The present invention also encompasses a construct comprising: (a) the DNA segment referred to above; and (b) a vector for introducing said DNA frament into a eucaryotic or procaryotic host cells. The vector utilized is, for example, Bluescript or pKK223-3. The vector may include a regulatory sequence operatively linked to said DNA segment. The vector may be, for example, Bluescript in which case the overall construct is designated as Pro1. The vector may also be, for example, pKK223-3 in which case the corresponding construct is referred to as pKKPRO.

The invention also includes a host cell stably transformed or transfected with the construct, such that an antiproliferative protein encoded by said construct is expressed. The host cell is a eucaryotic or procaryotic cell. A suitable procaryotic cell is, for example, an *Escherichia coli* cell. The protein which is produced is referred to as prohibitin. The construct utilized may be, for example, pKKPRO.

The present invention also includes a recombinantly produced protein or synthetic protein having all, or a unique portion, of the sequence of FIG. 3.

Moreover, the invention also encompasses a method of treating a condition in a patient characterized by an excess of cellular proliferation comprising, administering to said patient, an amount of an agent which binds to and enhances the function of prohibitin present in the cells of said patient sufficient to effect said treatment. In particular, one of the conditions which may be treated is, for example, cancer.

The invention also includes a method of treating a condition in a patient characterized by an excess of cellular proliferation comprising introducing in said patient a gene which expresses high levels of prohibitin in order to effect said treatment.

Another aspect of the invention is a method of treating a condition in a patient, characterized by insufficient cellular proliferation, comprising administering to said patient an amount of an agent which binds to and interferes with the function of prohibitin present in the cells of said patient sufficient to effect said treatment. The conditions to be treated include, for example, osteoporosis, fragile skin and poor wound healing.

The present invention also includes a method of treating a condition in a patient characterized by insufficient cellular proliferation comprising introducing into said patient an artificial gene that encodes an antisense messenger RNA of prohibitin in order to effect said treatment.

In addition, the invention also includes a pharmaceutical composition comprising prohibitin or a portion thereof, and a pharmaceutically acceptable carrier.

Top third of figure: the prohibitin cDNAs I1 and I12 are shown, with the common HindIII site (capital H and vertical bar) used to construct Pro1. Middle: the sequencing strategy is shown that was used to determine the nucleotide sequence of Pro1. The top two lines represent sequencing from the sense strand of Pro1 and the bottom two from the antisense strand. Each arrow represents a region of sequence read from a single primer. Bottom: the Pro1 cDNA is shown. The hatched box represents the open reading frame predicted from the nucleotide sequence (see also FIG. 3). Filled circles are the sites of the AATAAA polyadenylation signals. The capital "A"s refer to the poly (A) tail. The length in kilobits is shown at the bottom.

Figure 2:
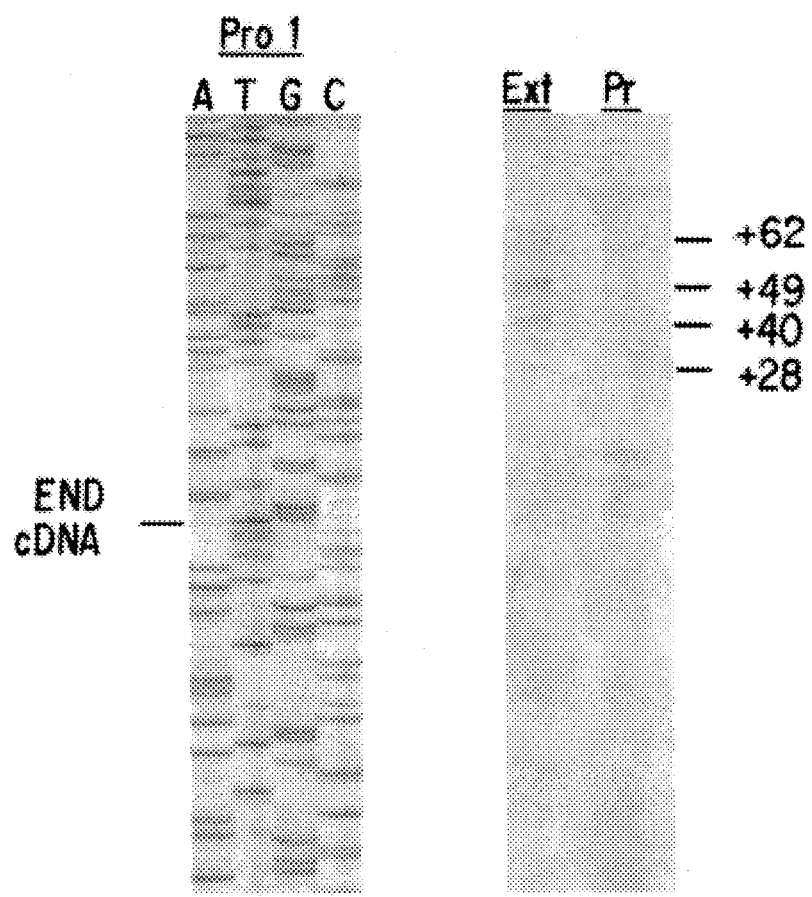

FIG. 2 shows primer extension analysis of transcript initiation. The primer extension products are shown that were produced by priming rat intestine poly(A) RNA with a 29 base oligonucleotide complementary to the Pro1 cDNA (Ext). At the left (Pro1) is a sequencing reaction using Pro1 cDNA as the template and the same 29mer as the primer. The latter is included as a size standard and the 5' end of the Pro1 cDNA is noted. An additional control (Pr) was the labeled primer alone to show that no material of large molecular weight was artifactually labeled. The numbering refers to the length in bases that the primed DNAs extend beyond the 5' end of the Pro1 cDNA.

FIGS. 3A–3B shows the nucleotide sequence of the Pro1 (see SEQ ID NO:1) cDNA. The DNA sequence of Pro1 is shown along with the translation of the longest open reading frame (see SEQ ID NO:2). The numbering is in basepairs. The AATAAA polyadenylation signals are boxed, as are the ATTTA mRNA stability motifs. The portion of Pro1 identical to M5 is overlined. Amino acids identical between the predicted gene products of the rat prohibitin cDNA and the Drosophila Cc cDNA are shown in bold italic type. The nucleotides of the region used to define oligonucleotides for microinjection are also shown in bold italic type.

Figure 4:
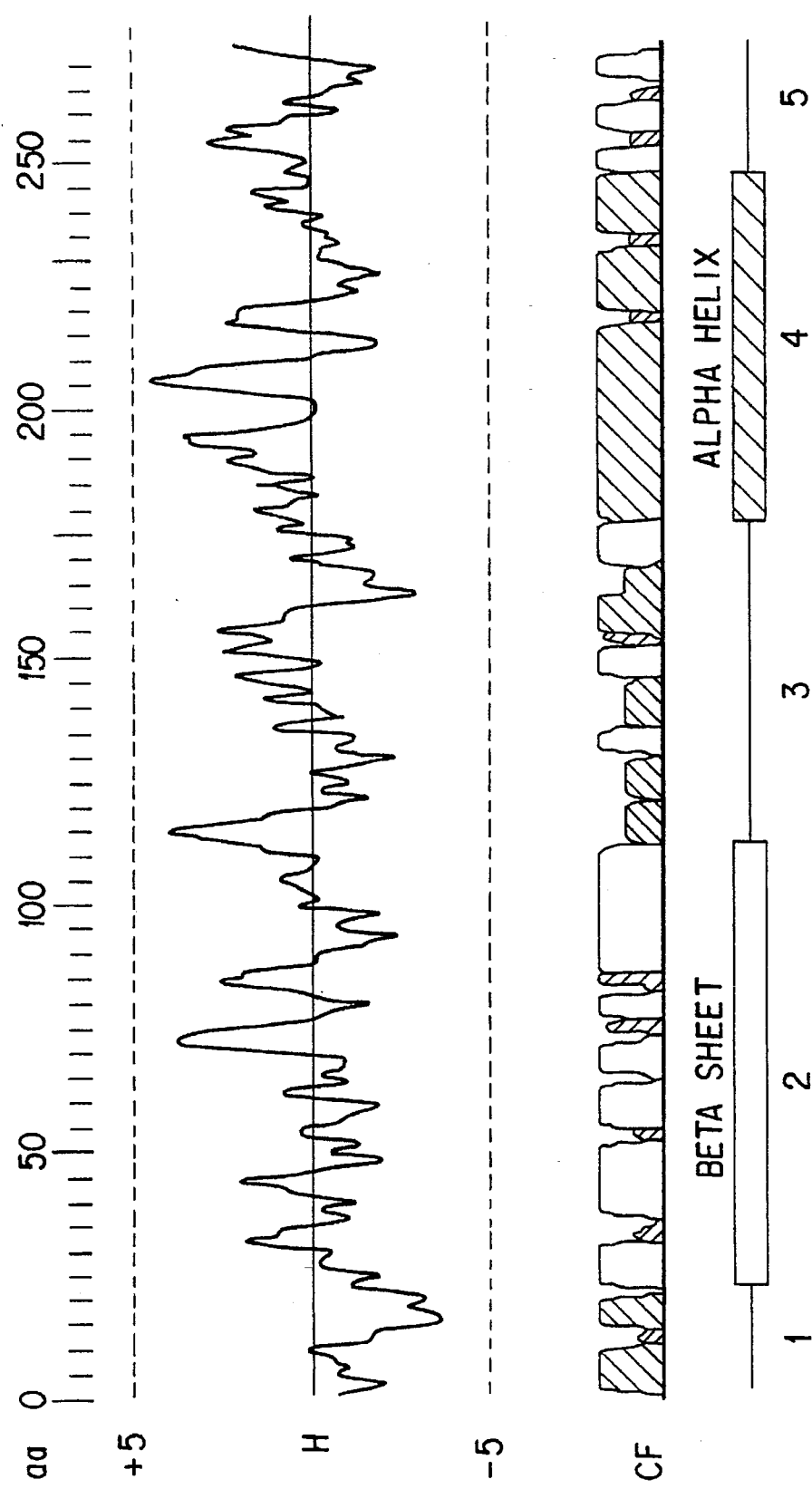

FIG. 4 shows secondary structure analysis of the prohibition ORF. At the top of the figure is shown a hydrophilicity profile (capital H) of the predicted amino acid sequence for the largest open reading frame found on the Pro1 cDNA. This plot was generated using the method of Hopp and Woods (Hopps et al., *Proc. Natl. Acad. Sci. USA* 78:3824–28 (1981)). A value of −5 indicates a strongly hydrophobic region, while +5 indicates a strongly hydrophilic region. The middle part of the figure shows the likelihood of formation of certain secondary structures along the length of the open reading frame, based on the criteria of Chou and Fasman (CF) (Chou et al., *Adv. Enzymol.* 47:45–147 (1978)). Regions predicted to be beta sheet are filled with white, those predicted to be alpha helix are gray, and predicted turns are black. A simplified version of this result is shown at the very bottom of the figure. The protein can be divided into 5 regions, of which only 2 and 4 have identifiable secondary structure.

Figure 5:
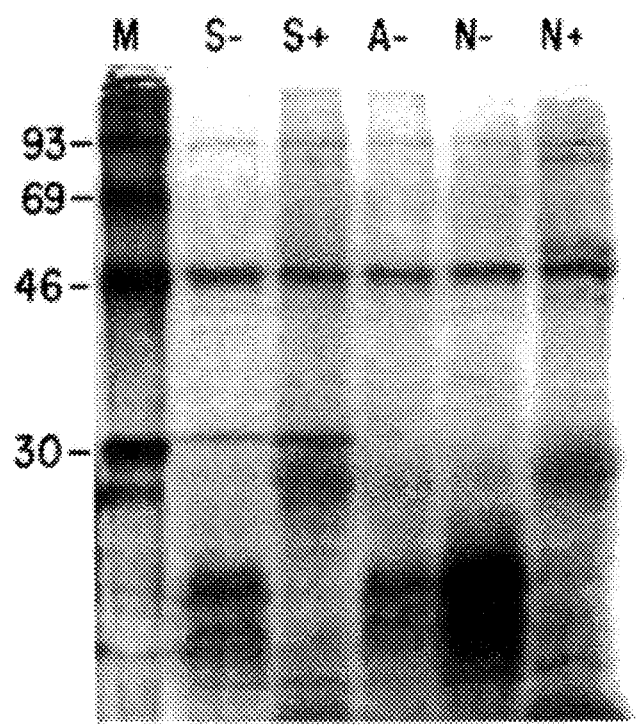

FIG. 5 represents in vitro translation of synthetic Pro1 mRNA. Shown are the products of several in vitro translation reactions. Proteins synthesized from RNAs endogenous to the reticulocyte lysate are seen in the no RNA lane (N−). When the sense transcript of Pro1 is synthesized in vitro and added to the in vitro translation reaction, one new band is seen at approximately 30 kilodaltons (lane S−). No new bands are observed when the antisense transcript of Pro1 is added as a control (lane A−). The same reactions were also run in the presence of canine microsomes (lanes marked with a +), but no alteration in the prohibitin specific and was seen (lane S+).

FIGS. 6A–6B represent a nucleotide sequence comparison of rat prohibitin (see SEQ ID NO:3) and Drosophila Cc cDNAs (see SEQ ID NO:4). The alignment that maximizes identity between the Pro1 cDNA and the Drosophila Cc cDNA is shown. The rat sequence is on the top of each strand pair. Only the region of the rat open reading frame is shown because homology falls off sharply outside this region. The numbering of the Pro1 cDNA is the same as in FIG. 3. The numbering of the Cc cDNA counts the first base of the full-length cDNA as base 1. The bold and italic regions in this figure are essentially the same as those shown in FIG. 3, specifically the regions of amino acid identify between the predicted open reading frames of the rat Pro1 cDNA and the Drosophila Cc cDNA. In this figure, however, it is the condon triplets that are so marked rather than the amino acids.

Figure 7:
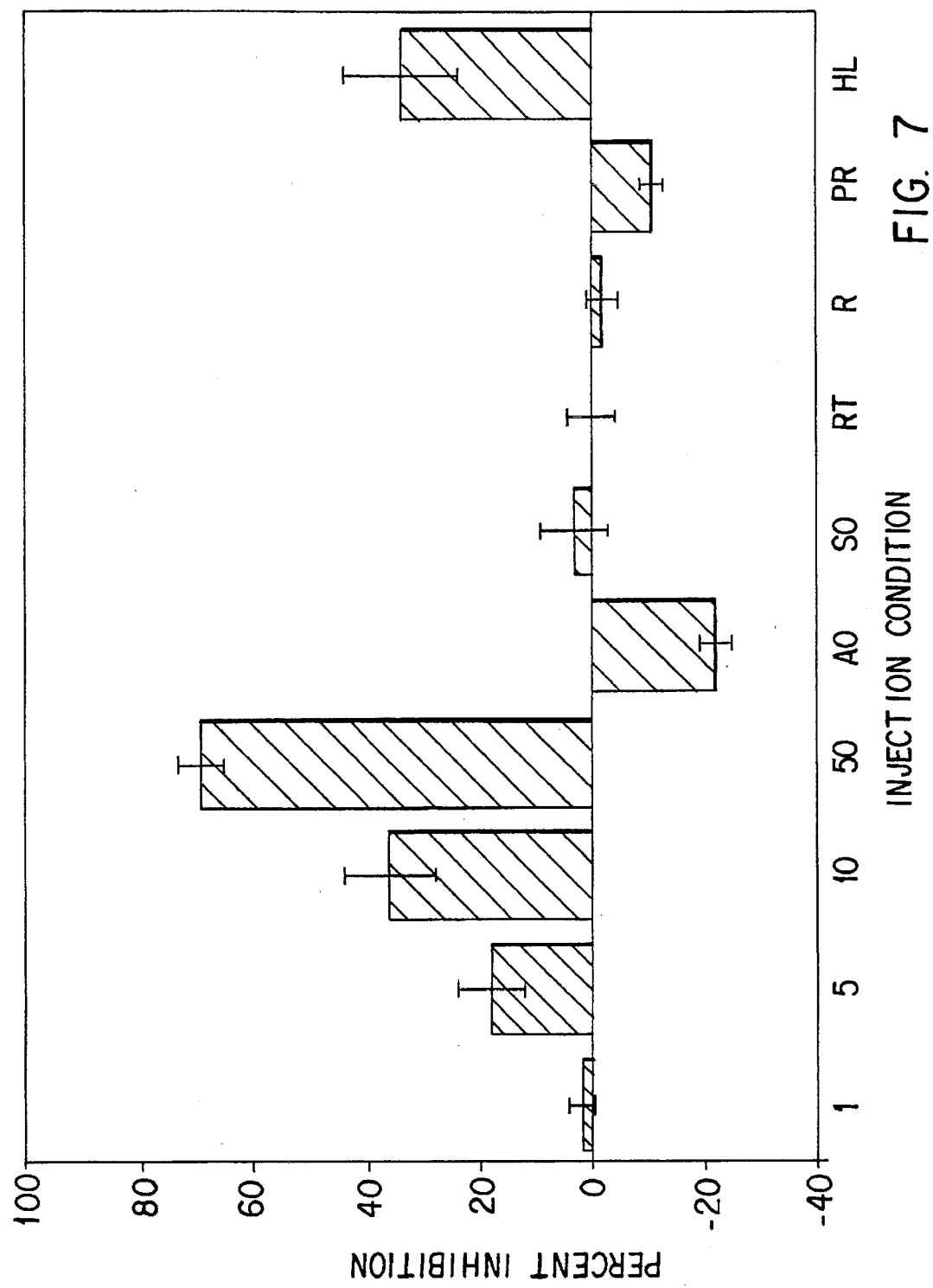

FIG. 7 represents the results of microinjection assays. Shown are the effects of microinjecting a variety of synthetic transcripts and oligonucleotides into normal human fibroblasts and HeLa cells. Percent inhibition was calculated as (U−I)/U×100, where U=percent labeled nuclei in uninjected cells and I=percent labeled nuclei in injected cells. A negative value therefore indicates stimulation of proliferation. The error bars show the standard error of the mean for three or more experiments. Symbols: 1, 5, 10, and 50 refer to the sense transcript of Pro1 injected at 1, 5, 10, 50 μg/ml respectively (all other transcripts were injected at 50 μg/ml); AO, antisense oligonucleotide (both oligonucleotides were injected at 1 mg/ml); SO, sense oligonucleotide; RT, RNase treated sense transcript; R, RNase alone; PR, prolactin sense transcript; HL, injection of Pro1 sense transcript into HeLa cells (all other lanes refer to normal fibroblasts).

Figure 8:
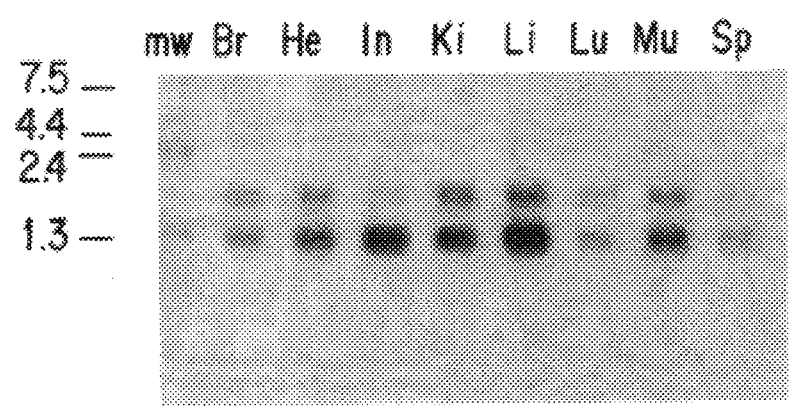
Figure 9B:
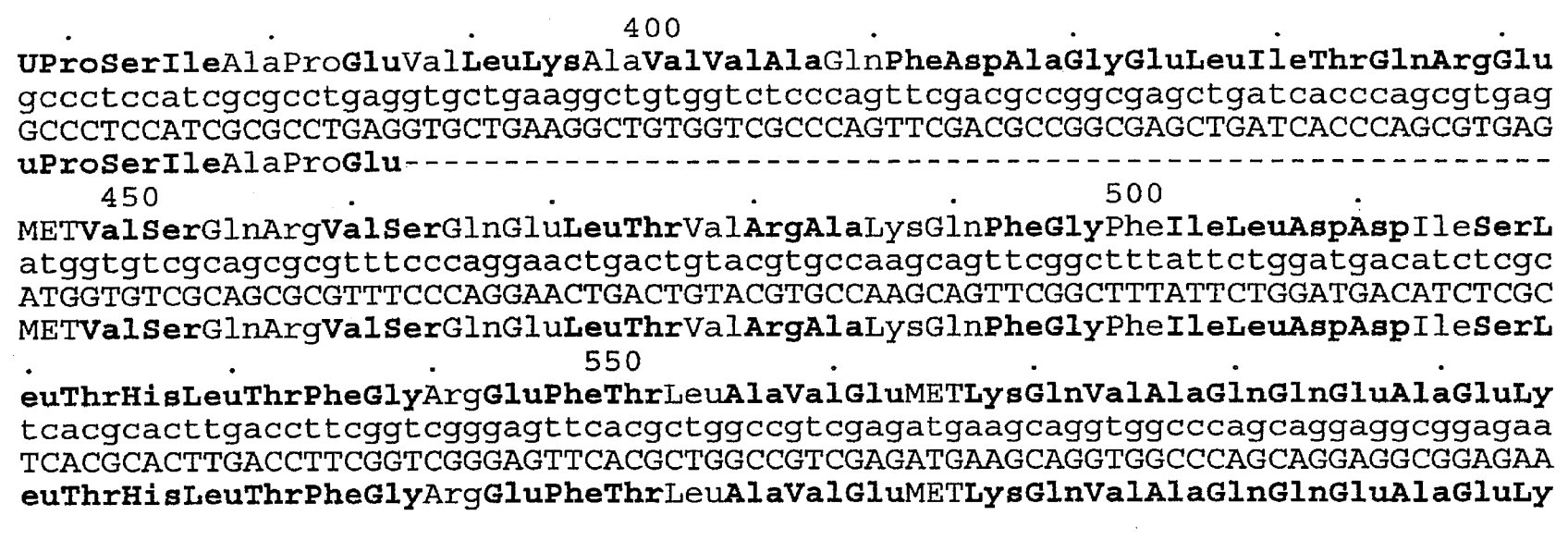

FIG. 8 shows the steady state expression of prohibitin mRNA in rat tissues. Northern hybridization of prohibitin gene expression is shown for eight rat tissues. 1.5 μg of poly(A) RNA from each organ was sized by electrophoresis, transferred to a filter, and hybridized with a fragment of the Pro1 cDNA extending from nucleotides 1 to 543 (FIG. 3). Symbols: mw, RNA molecular weight. standards (sizes given in kilobases); Br, brain; He, heart; In, intestine; Ki, kidney; Li, liver; Lu, FIGS. 9A–9C represent a comparison of the GENBANK Drosophila Cc DNA sequence (see SEQ ID NO:7) and the sequence of Drosophila Cc cDNA cloned by the present inventors (see SEQ ID NO:6). The sequence of a Drosophila Cc cDNA, DM4 was determined when it was ascertained that the sequence of the Cc DNA published in GENBANK was incorrect. Shown here is a comparison of the two versions of the sequence, with the nucleotide sequence in the middle and the translated amino acid sequences (see SEQ ID NO:5 and SEQ ID NO:8) on the outside of each line. Amino acid residues in bold are identical in Drosophila Cc or DM4 and rat prohibitin. Arrows below the GENBANK derived amino acid sequence identify positions where the Cc sequence is incorrect. The gap in the Cc sequence between nucleotides 386 and 444 is not an error, but rather a result of the isolation of two different cDNAs due to differential splicing of the primary transcript of the Cc/prohibitin gene during mRNA processing. A small portion of the cDNA sequences (residues 969–1024), which do not encode amino acids and which are identical in both sequences, have been omitted for clarity.

FIGS. 9B–9F represent a comparison of the rat, Drosophila, and S. cervevisiae prohibitin cDNAs (see SEQ ID NO:9, SEQ ID NO:11 and SEQ ID NO:13, respectively). That portion of the cDNA of the yeast analog of prohibitin which has been sequenced is presented, aligned with the corresponding region of the rat and Drosophila sequences. The degree of identity of the amino acid sequences (see SEQ ID NO:10, SEQ ID NO:12 and SEQ ID NO:14, respectively) is approximately %65 overall.

Figure 10:
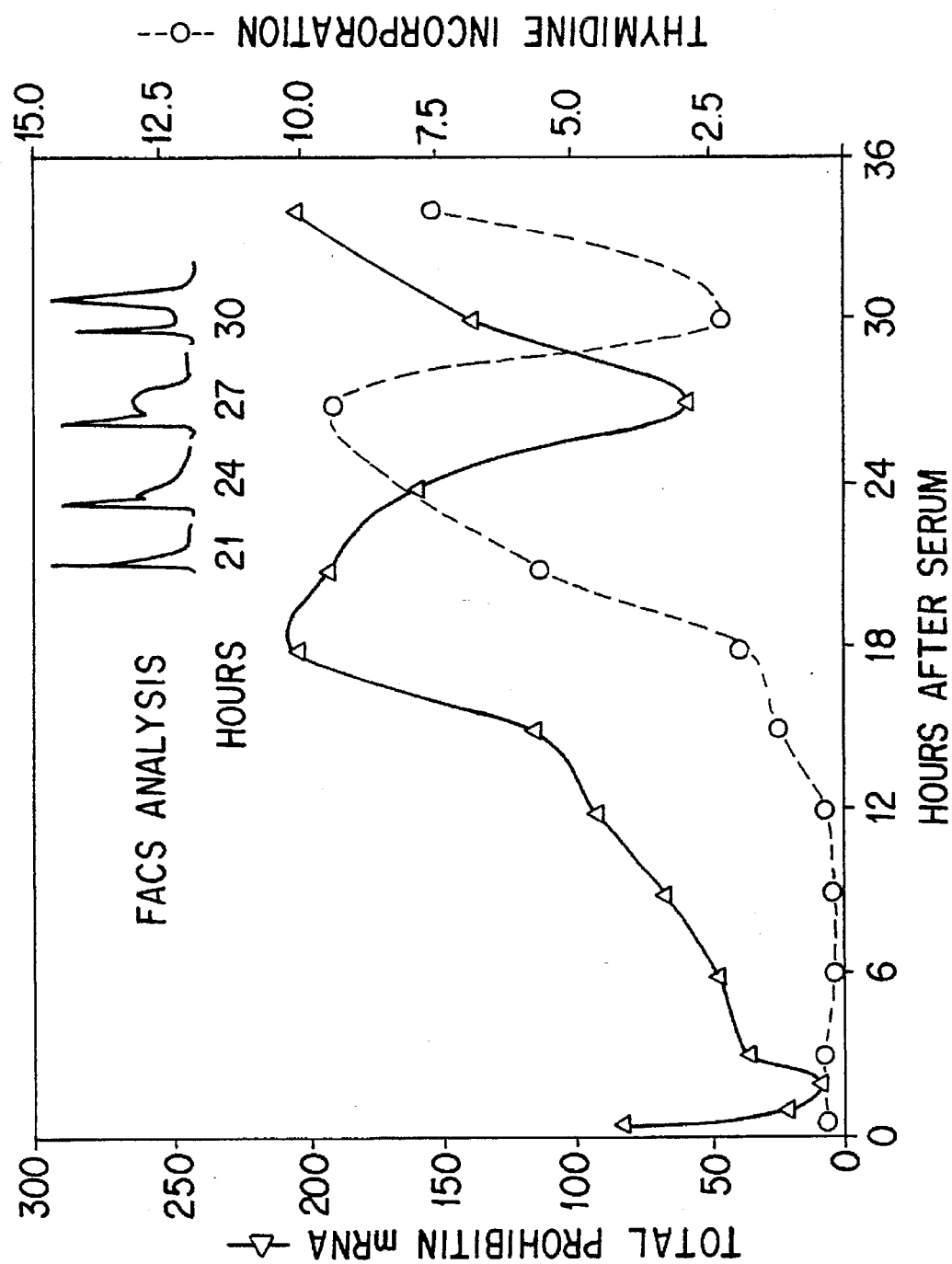

FIG. 10 shows that the level of prohibitin mRNA varies during the cell cycle. IMR-90 cells at PDL 22–24 were grown in DMEM supplemented with 10% fetal bovine serun (FBS) plus Gentamicin at 10 µg/ml/ At confluence, the cells were serum deprived in MCDB 104 medium for approximately 90 hours. Then the cells were stimulated with DMEM containing 10% FBS and finally harvested at various times. RNA was prepared from one aliquot of cells. $^3$H-thymidine incorporation (one hour pulse labeling) was measured from a second aliquot. A third portion of cells was stained with propidium iodide for analysis by fluorescence activated cell sorting (FACS). The level of both prohibitin mRNAs changes in concert, so the total combined mRNA level is shown. Within two hours of serum stimulation, the level of prohibitin mRNA falls from that in the starved cells to the minimum observed in the experiment. Between 2 and 18 hours, the amount of mRNA rises to a peak. The peak level of prohibitin mRNA, at 18–21 hours, is about threefold above the level in the starved cells and approximately twenty-fold above the minimum seen at two hours. Between 21–27 hours, the mRNA level falls to about one-forth of its peak, then begins to rise as a second cell cycle begins. In contrast, DNA synthesis, as measured by both FACS analysis and $^3$H-thymidine incorporation, is undetectable until 15 hours, peaks at 27 hours (near the minimum of prohibitin expression), and falls to a second minimum at 30 hours, then rises again until the end of the experiment. $^3$H-thymidine incorporation is presented as cpm×$10^{-3}$, and mRNA levels is in cpm, measured using a Betagen detector.

Figure 11:
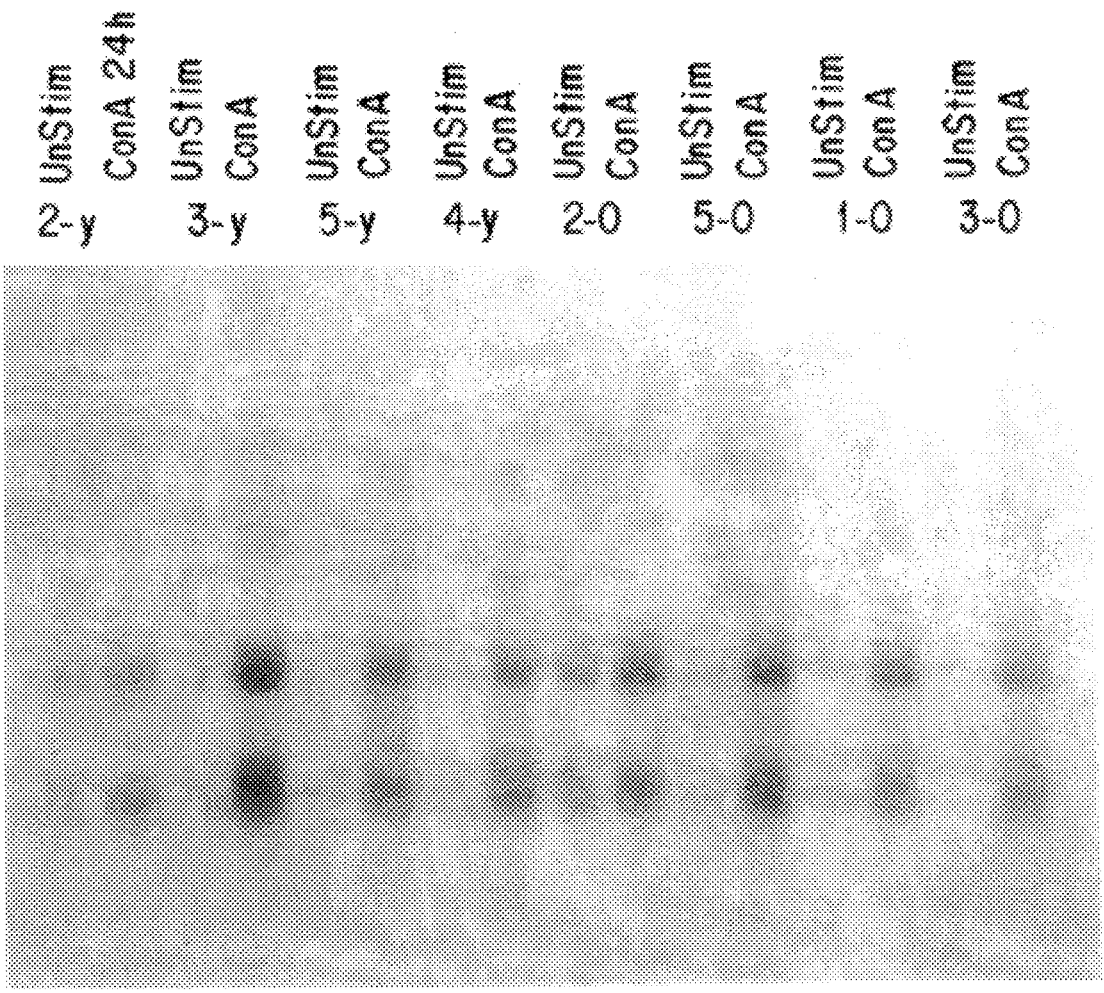

FIG. 11 shows that prohibitin mRNA is induced by concanavalin A stimulation of spleen cells. Whole rat spleens were minced and placed in RPMI 1640 medium supplemented with 10% heat inactivated fetal bovine serum, 2 mM glutamine, 20 mM Hepes, 50 µM 2-mercaptoethanol (complete medium). Single cells were obtained by sequential passage through 18, 20, and 22 gauge needles. Erythrocytes were lysed by treatment with 17 mM Tris, 0.74% NH$_4$Cl, pH 7.4. Cells were washed twice with complete medium, and $10^8$ cells were used in each experiment. Cells were grown in complete medium with or without the addition of concanavalin A to 5 µg/ml for 24 hours. At this time, the cells were collected by centrifugation, and RNA was prepared by standard procedures. 10 µg of total RNA was loaded in each lane and hybridized with a prohibitin cDNA probe. Preparations from eight individual rats are presented.

DETAILED DESCRIPTION OF THE INVENTION

The present invention relates to an intracellular protein with antiproliferative activity, referred to as prohibitin, and the uses thereof.

Prohibitin is neither microsomally processed nor secreted by the mammalian cell. Microinjection of its mRNA blocks DNA synthesis. More specifically, in both normal fibroblasts and HeLa cells, microinjection of a synthetic prohibitin mRNA blocks entry into S phase, whereas microinjection of an antisense oligonucleotide stimulates entry into S phase.

S phase is that portion of the cell growth cycle when DNA synthesis occurs. It appears that exogenous (artificially introduced) prohibitin can block cell proliferation in both normal and cancer cells, and that endogenous (naturally occurring) prohibitin has the same function. Thus, man-made alterations in the amount of prohibitin could be used to treat human syndromes (either specific diseases or more general abnormalities) that are based on an excess or an insufficiency of prohibitin. Syndromes that are due to an excess of proliferation, and perhaps an insufficiency of prohibitin, include the benign neoplasms and cancer. Syndromes that are due to an insufficiency of proliferation, and thus perhaps an excess of prohibitin, include many specific disorders associated with the aging process, such as osteoporosis, fragile skin, and poor wound healing. Impaired tissue regeneration is also associated with insufficient cellular replication. In addition, it is likely that many congenital malformations are due to either an excess or a deficiency of cell proliferation in developing tissues.

By sequence comparison, the prohibitin gene appears to be the mammalian analog of Cc, a Drosophila gene that is vital for normal development. In this regard, it is important to note that a complete loss of the Drosophila prohibitin equivalent (the Cc protein), results in a complete developmental failure; the organism dies during the transition from larva to pupa.

Another area in which prohibitin therapy might be of use would be in normal cells in certain specific contexts. For example, in parts of the body damaged by trauma (including heat and cold, radiation, physical disruption, and chemicals), the decision by the body to regenerate the tissue or form a scar can be thought of as a race for proliferation between connective tissue cells (such as fibroblast) and parenchymal cells (such as hepatocytes in the liver). In principle, regeneration rather than scarring might be favored by either increasing prohibitin in fibroblast or decreasing prohibitin in parenchymal cells.

The actual means by which increases or decreases in prohibitin might be achieved are potentially large in number. Having the sequence of the gene and the coding information for the protein available makes all such approaches possible. For example, in the case of congenital malformation in mice due to an excess or a lack of proliferation in certain cells types, it would now be possible in theory to correct this defect by creating transgenic mice with altered levels of prohibitin expression in these cells. To increase prohibitin levels, one may introduce a gene for prohibitin that expresses high levels of prohibitin; a tissue specific enhancer on the construct could be used to direct expression to the correct cell type. To decrease the level, an artificial gene that makes a complementary copy (antisense mRNA) of prohibitin may be introduced instead, with the tissue specific enhancer if needed. Such technology has not yet been applied to human beings but this is due to an uncertainty about side effects, and for ethical reasons, not because of technical limitations.

Having the predicted protein sequence of prohibitin and knowing that it is a key antiproliferative protein also makes it possible to begin designing pharmaceuticals that would be able to enhance or interfere with its function. For example, one may first test a variety of chemicals for their ability to bind to prohibitin with high affinity. Such testing might involve the use of a synthetic prohibitin, made in large amounts in bacteria, which would be dependent on the availability of a prohibitin cDNA as described herein. Those that did show such binding could then be used to define related structures that might bind even more tightly. Final candidates that showed both strong and specific binding could then be assayed in tissue culture cells to determine their effect on cell proliferation. Such approaches have already been successful in defining a wide variety of medicines specific for other biomolecules that can be taken in oral form and which have profound effects on cell function because of this interaction at the molecular level. Such pharmaceuticals could be used to accomplish the modulations of prohibitin defined above. Efficient and directed approaches to their isolation are completely dependent on the identification of prohibitin as a key target for intervention in cell growth and an understanding of the structure of the protein.

Thus, in view of the above, a patient having a condition characterized by an excess of cellular proliferation could be treated with an agent (perhaps in oral or injectable form) that binds to prohibitin present in the cells of the patient and enhances the function of this protein. In contrast, a patient having a condition characterized by an insufficiency of cellular proliferation could be treated with an agent that binds to prohibitin and interferes with its function. In addition, with respect to the treatment of disorders involving excess cellular proliferation, a composition could be administered to the patient which comprises prohibitin or a portion thereof, and a pharmaceutically acceptable carrier.

The prohibitin cDNA sequence is presented in FIGS. 3A–3D. The protein coding portion of the cDNA is noted by the translation into amino acid sequence below the nucleotide sequence. The amino acid sequence of the prohibitin protein is conserved evoluntionarily, as homologous sequences from human, rat, Drosophila (Cc) and yeast have been isolated. The finding of a prohibitin-like protein in yeast implies that the gene plays an important role in regulating eukaryotic cell growth, as yeasts are considered to be representative of the common ancestor of all other eukaryotic cell types. The areas of sequence homology among the four sequences that have been obtained are not clustered, but rather extend along the entire length of the protein. The implication is that almost all of the protein is important for its function. The evolutionary evidence suggests that many compositional changes are possible that still produce a functional protein. Site-directed mutagenesis experiments, which change individual (or small groups) of amino acids and then assess the functionality of the mutated gene product, can be utilized to determine the degree to which the composition of small regions can be changed and still produce functional proteins. Such experiments will be undertaken in the near future.

The gene which encodes prohibitin is currently being sequenced by the present inventors. (The cDNA sequence in FIG. 3 represents the mRNA sequence, which cells utilize directly to produce prohibitin protein. The gene for prohibitin represents the "blueprint" for producing prohibitin mRNA. The "plan" is transcribed into mRNA through a complex process. The sequence of the complementary DNA, of course, gives the predicted amino amino sequence for prohibitin.) It appears that several forms of prohibitin mRNA exist in cells, generated through processes called "differential splicing" and "differential polyadenylation". The functionality of and developmental expression of the various forms will be investigated sometime. It is possible that several slightly different forms of prohibitin mMRNA will prove to be functional in cells.

With respect to the cloning and analysis of prohibitin cDNA, the initial isolation of a small piece of prohibitin cDNA is described in McClung et al, supra. (The strategy utilized for this purpose is described in Nuell et al., *Exper. Gerontol.* 24:4696–76 (1989).) The present invention includes the isolation and characterization of the longer prohibitin cDNA containing the complete protein coding sequence.

In summary, a differential colony hybridization approach was used to isolate cDNA clones, prepared from normal rat liver mRNA size-selected to approximately 2 kilobases, whose expression was higher in normal rat liver than in regenerating rat liver. A number of clones were picked, several of which were found to represent genes whose expression is known to decline during liver regeneration. Three clones with the desired expression characteristics did not match to any known sequences. Plasmid DNA from these three clones was produced in large amounts and attached to a solid support. The derivatized support was then used to purify mRNA representing the plasmid sequences (a process called hybrid selection) and the purified mRNA was assayed for the desired biological activity by microinjection into serum-starved fibroblasts and then assaying DNA synthesis following serum-stimulation of the cells. One of the three clones tested, M5, had activity in this assay; mRNA purified using M5 as the substrate enriched antiproliferative mRNA eight-fold over the activity in starting material. M5 was then used as a probe against a commercially available rat intestine cDNA library. Two clones were isolated by standard plaque hybridization procedures and characterized. I12 was found to contain a potential translation initiation amino acid (methionine) and a long "open reading frame", a potential protein coding region. I1 was found to contain the same long open reading frame and a polyadenylated region indicating the end of the functional mRNA, but no initiating methionine. Thus, I1 was attached to I12, using a shared restriction enzyme site (HindIII), to produce the Pro1 plasmid drawn in FIG. 1. Pro1 was used as a template to synthesize prohibitin mRNA in Vitro using T3 RNA polymerase. The sequence of the prohibitin cDNA and the initial analysis of its biological activity and expression are described herein. In FIG. 7, it is shown that inhibition of DNA synthesis is obtained in normal fibroblasts following microinjection of prohibitin mRNA directly into the cells. Higher doses give stronger inhibition. In addition, the antiproliferation activity is abolished by treatment of the sample with an RNA-degrading enzyme prior to microinjection. Interference with function of the endogenous mRNA by injection of an antisense oligonucleotide results in a stimulation of DNA synthesis. The last result in the figure shows that administration of prohibitin mRNA to HeLa cells, a type of cancer cell, is also able to inhibit DNA synthesis. FIG. 3 shows the complete nucleotide sequence of the prohibitin cDNA used in the assay in FIG. 7. The portion of the cDNA that encodes the protein extends from nucleotide 11 to 830, and the translated amino acid sequence in shown. The homologous sequences from Drosophila and the portion of yeast sequence that we were obtained are shown in FIGS. 9D–9C.

Two sizes of prohibitin mRNA are found in each tissue that have been examined. Results from the investigation of eight tissues are presented in FIG. 8. The amount of prohibitin mRNA is found to fluctuate during the cell growth cycle; this is illustrated in FIG. 10. For this figure, a fibroblast cell population was synchronized by serum deprivation for 96 hours and then stimulated with 10% fetal bovine serum. At various times, the amount of prohibitin mRNA and the concurrent amount of DNA synthesis were assessed. Immediately after serum stimulation, prohibitin mRNA declines, then rises to a peak level in G1, a period of the cell cycle when DNA precursors are being synthesized by the cells. As the cells actually begin DNA synthesis, prohibitin mRNA declines, reaching a low level at the peak of DNA synthesis. The amount of prohibitin mRNA begins to rise again at the completion of DNA synthesis. A similar experiment conducted using regenerating rat liver tissue shows a similar pattern of expression. FIG. 11 shows the result of a determination of prohibitin mRNA levels in spleen cells in culture, unstimulated and treated with concanavalin A, which stimulates them to divide. Untreated cells demonstrate a low level of prohibitin mRNA, while cells treated with mitogen demonstrate a five to tenfold increase in prohibitin mRNA. This result, combined with the results of the serum stimulation experiment, suggest that prohibitin mRNA is present at low but detectable levels in quiescent cells, but is induced to higher levels in a cycling population. Thus, Pro1 cDNA can be used in some situations as a diagnostic probe to determine if a cell population is quiescent or cycling.

The present inventors have recently localized the prohibitin gene to a specific region on chromosome 17 (from q21 to q22). They have also shown that human populations have a high frequency of both the presence and the absence of a specific EcoRI site within the prohibitin gene, part of which has been cloned. Such a site is called a "restriction fragment length polymorphism," and can be used to follow the transmission of a specific gene region from parent to child in families. Thus, in principle, prohibitin and this prohibitin-related EcoRI site could be used to predict whether any individual had received a particular form of the prohibitin gene or a nearby gene from their parents. If prohibitin or a nearby gene were someday shown to be related to a specific inherited disease, the availability of the prohibitin DNA sequence and this EcoRI site would be important in the genetic testing of unborn babies for this disease. Currently, there are several genes partly identified that prohibitin probes may help track in this way; the chromosomal region where prohibitin is located has been shown to undergo rearrangements in some types of leukemias and is part of a region found rearranged in some breast tumors.

Antibodies have been used in both biochemical fractionation experiments and in immumocytostaining studies to determine the location of prohibitin protein in cells. It has been determined that the protein is not secreted from cells in tissue culture and that within the cell it can be found in both the cytoplasm and the nucleus. Preliminary studies suggest, but have not proven, that the location of prohibitin in the cell varies during the cell cycle.

In addition to the uses for Pro1 cDNA mentioned above, it may also be used as a direct therapeutic agent. The intracellular location of prohibitin provides a challenge to delivery of prohibitin protein to diseased cells, but three strategies can be envisioned. The first involves the incorporation of prohibitin protein into liposomes. Prohibitin protein (produced by any technology) could be packaged into liposomes designed to fuse with the membranes of diseased cells and thus deliver the prohibitin to the cytoplasm. In such a delivery system, it may be necessary to modify the prohibitin sequence so that it will be able to survive cellular processes that occur during such membrane fusion events.

The second strategy involves the creation of a targetor-effector fusion protein. The prohibitin cDNA sequence may be spliced, by recombinant DNA techniques, onto other (targetor) protein sequences that function to cause binding of the "fusion protein" to a particular (diseased) cell type. Alternatively, the functional peptides may be joined by chemical linkage. The chimeric protein is then endocytosed by a mechanism determined by the targetor sequences, and the prohibitin "effector" sequences are delivered to the cytoplasm of the targeted cell. Again, the sequence of prohibitin may need to be modified or truncated to allow for effective delivery. It should be noted that a few laboratories are trying this approach using the physical attachment of toxic molecules to polypeptides conferring specific binding properties, such as antibodies. In a related technique, radioactive isotopes have been used to tag tumor specific antibodies to provide low dose radiation therapy directly at the site of tumors rather than administering high doses from outside the body.

The third strategy involves expression from a corrective DNA construct or "gene therapy." Prohibitin cDNA may be incorporated into a recombinant DNA molecule designed to express prohibitin protein in a specific cell type, diseased or otherwise, introduced into that cell type for purposes of "gene therapy."

Pro1 cDNA may also be utilized as a diagnostic probe for genetic diseases linked to 17q21–22. The chromosomal localization of prohibitin to the region 17q21–22 implies that it may be used as a restriction fragment length polymorphism probe for diseases resulting from deletion or rearrangement of this and nearby regions of the chromosome. Such rearrangements have been implicated in the etiology of acute myelogenous leukemia. Deletion or rearrangement of the region 17cen to 17q23 has been noted in several breast tumors as well. Future work may demonstrate a diagnostic or prognostic link with prohibitin in these diseases. It is possible that rearrangements of prohibitin itself will be found to influence the initiation or progression of other tumor types as well.

Additionally, Pro1 cDNA may be used as a diagnostic probe for proliferative disorders. The finding that prohibitin is expressed at high levels in spleen cell populations that are cycling versus quiescent spleen cells suggests that prohibitin might be used as a DNA probe diagnostic for general failure of this cell type to proliferate in response to mitogens. Alternatively, an excess of proliferation might be monitored.

Furthermore, another therapy related to prohibitin involves the use of an antisense oligonucleotide which stimulates cell division. More specifically, injection of an antisense oligonucleotide that can hybridize to prohibitin mRNA normally present in cells will stimulate them to divide. It is possible that some condition will be found where normal or abnormal prohibitin action prevents desirable cell proliferation either in vitro or in vivo. In such instances, it is conceivable that administration of antisense oligonucleotide to the cells will abolish the activity of prohibitin and allow the desired proliferation.

With respect to the production of the prohibitin protein in large quantities, several systems currently exist for the production of large amounts of rare proteins by expression of the cDNA in other organisms. One such system is currently being tested to express the prohibitin cDNA utilizing a bacterial host.

The Pro1 construct, as it exists, is very useful for site-directed mutagenesis experiments, as the vector used, for example, Bluescript, is designed to allow production of templates for these experiments. Mutated Pro1 plasmids can serve as a substrate for in vitro synthesis of mutant prohibitin mRNA which could be tested directly for activity in the microinjection/DNA synthesis assay described herein. Such experiments will be valuable in determining which amino acids are necessary for prohibitin action. This may be an aid in the design of drugs that will interact with prohibitin and that may therefore serve as medicines for proliferative disorders.

The prohibitin cDNA or gene may prove to be useful in the creation of cell lines which overproduce prohibitin by transfection with an appropriate recombinant DNA plasmid or virus. Such experiments are currently being undertaken. Such strains should be useful in investigating other elements in the pathway by which prohibitin exerts its action. Cell lines underproducing prohibitin are in principle easy to produce as well, now that the cDNA has been cloned. One approach would be to introduce a genetic construct that would produce an antisense prohibitin mRNA (analogous to the microinjection of the antisense oligonucleotide described above); another would be to use recombination between the endogenous prohibitin gene and an introduced gene to disrupt the endogenous gene. Both technologies have already been used successfully in analogous experiments with other genes. Cells that over or underproduce prohibitin should be useful in screening for pharmeceuticals that can compensate for such alterations in prohibitin levels. Such drugs should be useful as medicines for the treatment of disorders based on either under or overproliferation, as described above.

The nucleotide sequence of the prohibitin cDNA may be used to derive the amino acid sequence of the prohibitin protein. Portions of the sequence useful for the production of antibodies may be predicted by analysis of the probability of surface localization of stretches of the amino acid sequence. The corresponding peptides be synthesized in vitro and used as immunogens to raise antibodies specific to the prohibitin protein. Such antibodies have been produced in for use as a research tool (see description of the cDNA) for the analysis of prohibitin. Such antibodies may also be used as reagents to purify prohibitin from complex mixtures such as tissue homogenates or cultured cell lysates.

The production of the actual prohibitin protein is described in Example XI below. Basically, the genetic sequence encoding cDNA is inserted into a vector, for example, pKK223-3, and this construct which may be referred to as pKKPRO, for example, is then inserted into a host cell. The host cell utilized may be, for example, an $E.$ $coli$ cell. The host cell expresses the prohibitin.

The present invention can be illustrated by use of the following non-limiting examples.

EXAMPLE I

Figure 1:
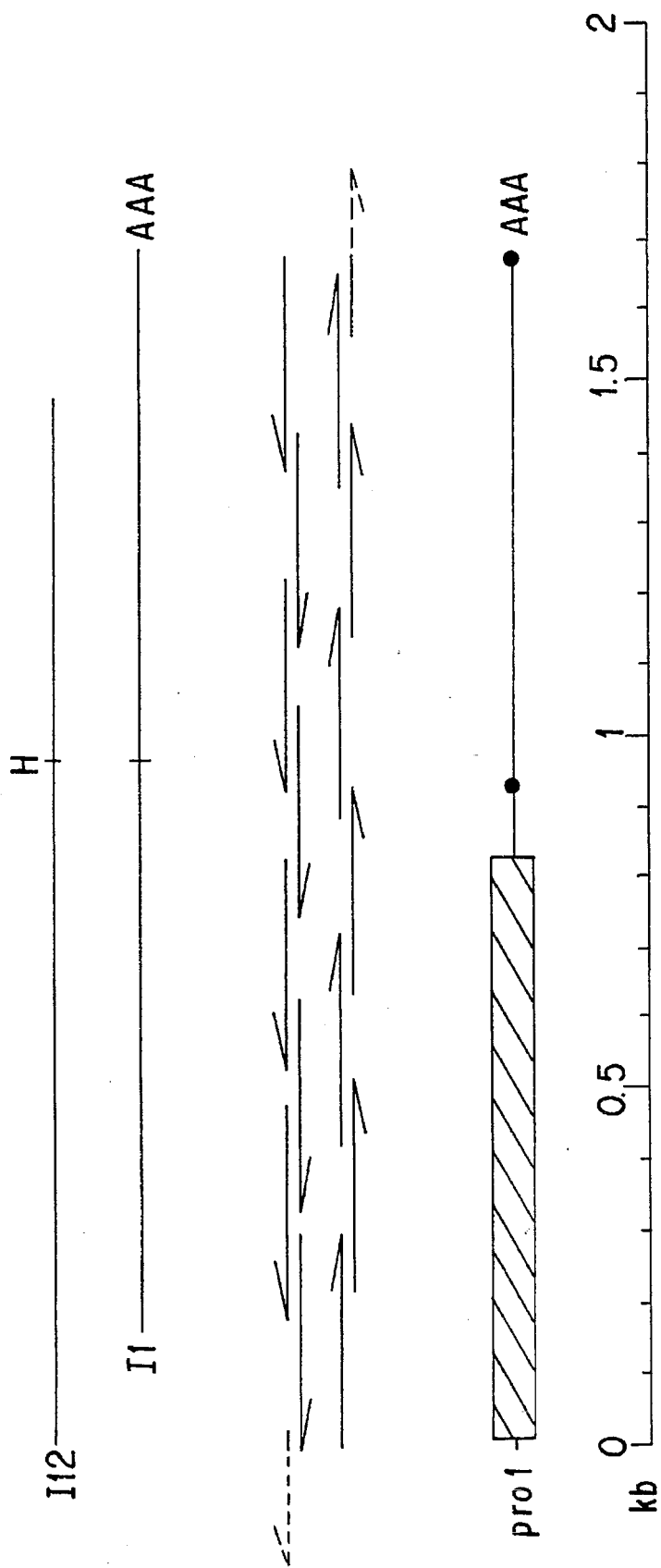
FIG. 1 represents the cloning and sequencing strategy for prohibition complementary DNAs (cDNAs).

Cloning and Construction of the Pro1 cDNA and Determination of the Nucleotide Sequence $6 \times 10^5$ clones from a rat intestine cDNA library in the LambdaZapII vector (Stratagene) were plated on $E.$ $coli$ strain XL-1 Blue and screened by plaque hybridization using standard techniques (Maniatis et al., Molecular Cloning: A Laboratory Manual, pp. 320–21 (1982). Hybridization was performed at 42° C. in 50% formamide hybridization buffer (50% formamide, 5× Denhardt's solution, 5× SSPE, 0.1% SDS, 100 μg/ml denatured, salmon sperm DNA). Equivalent hybridization conditions, e.g. 68° C. in an aqueous hybridization buffer, can also be used. The PstI insert from the M5 cDNA (McClung et al., supra) was labeled by random primer extension and used as probe (Feinberg et al., Anal. Biochem 132:6–13 (1983)). Plasmids were derived from positive clones using the in vitro excision procedure provided with the library. Clone I1 extends from nucleotide 162 of FIG. 3A to a poly (A) tail of 30 bp. Clone I12 extends from nucleotide 1 to nucleotide 1480 of FIGS. 3A–3D. To construct the Pro1 clone, both plasmids were cut with HindIII. The fragment of I12 containing the Bluescript plasmid and initial 970 bp of prohibitin, and the fragment of I1 comprising the 3' 718 bp of prohibitin and the poly (A) tail were gel purified and ligated to obtain the Pro1 cDNA. Pro1 encodes a complete open reading frame of 272 amino acids and a long 3' untranslated region. This region contains two potential polyadenylation sites, two ATTTA motifs that have been implicated in the control of mRNA stability (Shaw et al., Cell 46:659–67 (1987)), and a 30 base poly(A) tail. The Pro1 cDNA lies between a T7 and a T3 promoter in the vector, so it can be transcribed in either orientation in vitro. To rule out any cloning artifact, the DNA sequence of Pro1 was obtained (in addition to the sequences of I12 and I1) using the priming sites shown (FIG. 1).

EXAMPLE II

Primer Extension

Primer extension analysis of the transcript initiation site of prohibitin was performed essentially as in the method of Dean et al., Dean et al. teach annealing of the oligonucleotide to the mRNA in 250 mM KCl, 2 mM Tris-HCl pH 7.9, 1 mM vanadyl ribonucleoside complex. Dean et al. describe annealing at five different temperatures, 37° C., 43° C., 48° C. 55° C. and 60° C., to ensure that the optimal temperature for the oligonucleotide is reached. Vanadyl ribonucleoside complex was omitted from the reaction (Dean et al., Nucl. Acids Res. 15:4655–68 (1987)). An HPLC purified synthetic oligonucleotide complimentary to nucleotides 131 to 159 of Pro1 (see FIG. 1) was used to prime cDNA synthesis from 10 μg of poly(A) RNA prepared from rat intestine. Pro1 cDNA sequenced with the same primer was used as a molecular weight standard. Products were separated on a 6% sequencing gel and autoadiographed using Kodak XAR-2 film.

To determine how much 5' untranslated mRNA was missing from the hybrid cDNA clone, primer extension studies were performed. A 29 base oligonucleotide complementary to prohibitin mRNA (positions 131 to 159; see FIG. 1) was used to prime rat intestine poly(A) RNA (FIG. 2). Four primer extension products were identified, 28, 40, 49 and 62 bases longer than the 5' end of the Pro1 cDNA.

EXAMPLE III

Nucleotide Sequences and Predicted Amino Acid of Pro1
DNA Sequencing:

CsCl purified preparations of plasmid DNAs were sequenced using the Sequenase 2.1 kit from U.S. Biochemicals and synthetic primers purchased from the Midland Certified Reagent Company. The entire Pro1 cDNA was sequenced on both strands.
Computer Analysis of Sequence Data:

The GenBank release current on May 11, 1990 was searched for DNA sequences homologous to Pro1 using the FASTA algorithm (Pearson et al., Proc. Natl. Acad. Sci. USA 85:2444–48 (1988)).

The predicted amino acid sequence of the largest open reading frame was determined from the nucleotide sequence (FIG. 3). Using the QUEST program against the KEY-BANK database on BIONET, this amino acid sequence was searched for a variety of protein motifs, including ATP binding sites, nuclear localization signals, transcription factors (leucine zipper, helix-turn-helix, homeobox), and signal sequences. No matches better than those for random sequences were found. There are two potential glycosylation sites (Asn-X-Thr or Asn-X-Ser), but in the case of prohibitin, these are apparently not utilized (FIG. 5).

EXAMPLE IV

Secondary Structure Analysis of the Predicted Protein

To search for possible transmembrane regions, the predicted amino acid sequence was subjected to a hydrophilicity analysis using the method of Hopp and Woods (Hopp et al., supra). None were found (FIG. 4). The method of Chou and Fasman was applied to identify potential elements of secondary structure (FIG. 4) (Chou et al., *Adv. Enzymol.* 47:45–147 (1978)). Prohibitin can be divided into five structural regions on this basis. Region 2, in the N-terminal half, is a large region of beta sheet. Region 4, in the C-terminal half, is a large region of alpha helix.

EXAMPLE V

In Vitro Transcription

For transcription in the sense of orientation, the Pro1 cDNA was linearized with ApaI and transcribed from the T3 promoter of the Bluescript vector. Transcription was performed using a kit purchased from Stratagene using the conditions for large scale preparation of capped RNA given in the "Protocols and Applications Guide," pp. 43–45. This manual is available upon request from Promega Biotec, Madison, Wis. The 5' cap analog was purchased from Boehringer Mannheim. Transcription was performed for one hour at 37° C. after which the amount of polymerase and nucleotide was increased by 50% and transcription continued for an additional one to two hours. For the prolactin control mRNA, plasmid Pr1, containing a complete prolactin cDNA (Stewart et al., *Endocrinology* 126:773–78 (1990)) was linearized with BglII and transcribed as above, but using SP6 polymerase.

EXAMPLE VI

In Vitro Translation of a Synthetic Prohibition mRNA

The predicted open reading frame of Pro1 encodes a protein product of approximately 30 kilodaltons that has two potential N-glycosylation sites. To verify the existence of this reading frame, prohibitin RNA synthesized in vitro from Pro1 was translated in vitro (FIG. 5). Translation of the lysate, with no added synthetic RNA, produced a number of control protein bands unrelated to prohibitin (lane N–). Translation of a sense transcript (lane S–) produced one additional protein band of approximately 30 kilodaltons, as expected. No additional products were observed upon translation of an antisense transcript (lane A–). To test the use of the N-linked glycoslyation sites, canine microsomes were added during a set of translation reactions (lanes marked with a +). This did not result in a change in mobility of the 30 kilodalton band, as might be expected from sugar addition. Other changes in size attributable to signal sequence removal or other protein cleavage events were also not observed. These data suggest that prohibitin is an intracellular protein, as expected from the fact that it is active when its mRNA is microinjected into cells. Further confirmation of this conclusion has recently been obtained by Western blot analysis, which shows prohibitin in lysates of cultured cells but not in culture supernatants (data not shown).

The Pro1 synthetic mRNA was translated using a reticulocyte lysate kit, including canine pancreatic microsomes, purchased from Promega Biotec, using the protocol provided with the kit. $^{35}$S-methionine and $^{14}$C-leucine were purchased from Amersham. Protein samples were separated on precast 12% SDS-PAGE gels (NOVEX). The gels were treated with a fluorographic enhancer (New England Nuclear) and exposed to Kodak XAR-2 film.

EXAMPLE VII

Microinjection Assay for Antiproliferative Activity

Microinjections were carried out and assayed as described (McClung et al., supra). Human diploid fibroblasts from neonatal foreskin (CF-3) were grown on coverslips, then growth arrested by serum starvation (0.1%) for one week. Following microinjection (200–400 cells injected per experiment), the cells were stimulated with serum (10%) and exposed to $^3$H-thymidine for 24 hours, then fixed and processed for autoradiography. The concentration of transcript was 50 µg/ml unless otherwise noted. Oligonucleotides were injected at 1 mg/ml. HeLa cells were treated identically except they were not placed in low serum. Percent inhibition was calculated as (U–I)/U×100, where U=percent labeled nuclei in uninjected cells and I=percent labeled nuclei in injected cells. A negative value therefore indicates stimulation.

To demonstrate the antiproliferative activity of prohibitin mRNA, Pro1 was transcribed in vitro, and the synthetic mRNA was microinjected into normal human fibroblasts (FIG. 7). A 69% decrease in the number of nuclei labeling with tritiated thymidine was observed, compared to an uninjected population. Dose-response experiments demonstrated a half-maximal antiproliferative effect upon injection of approximately 240 RNA molecules per cell (calculated from amount injected, concentration injected, and molecular weight). A synthetic rat prolactin mRNA (Stewart et al., supra) caused an 11% increase, indicating that inhibition is not produced by every mRNA. Prohibitin mRNA also caused a 34% inhibition of HeLa cell DNA synthesis, indicating that prohibitin can arrest replication in these cancer cells.

Control experiments with RNAse digested sense transcript showed that, as expected, the antiproliferative effect was dependent on intact prohibition mRNA (FIG. 7). Microinjection of RNAse alone had no effect on proliferation, making it clear that the RNAse acted by degrading prohibitin mRNA rather than by providing a canceling proliferative stimulus.

To demonstrate a physiologic antiproliferative role for prohibitin, an 18 base oligonucleotide was injected to bind endogenous prohibitin mRNA and block its activity. This antisense oligonucleotide caused a 22% increase in the number of nuclei incorporating thymidine (FIG. 7). Control injection of the corresponding sense oligonucleotide produced a 3% decrease in labeled nuclei. These data suggest that prohibitin and its mRNA are normally present in fibroblasts and play a role in regulating proliferation.

Microinjected cells showed no evidence of any toxic effect. No abnormal morphologic changes were observed in this regard, such as rounding or detachment. Viability of microinjected cells was over 95% as assessed by cell number 24 hours after injection. Surviving microinjected cells could all re-enter S phase (data not shown).

EXAMPLE VIII

Expression of Prohibitin mRNA In Vivo

One might expect that a gene playing a central role in the regulation of cell proliferation would be expressed in most adult cell types. To test this idea, mRNA as extracted from a number of rat tissues and analyzed by Northern hybridization (FIG. 8). RNA was prepared from dissected rat tissues by disruption in guanidine isothiocyanate and CsCl ultracentrifugation, then enriched for poly(A) RNA by a single pass over oligo-dT cellulose, with only minor modifications of the standard procedures as described in Maniatis et al., *Molecular Cloning: A Laboratory Manual*, pp. 196–98 (1982). RNA concentration was determined by absorbance at 260 nm and equal quantities were loaded on a gel for Northern blotting. A fragment of the Pro1 cDNA extending from nucleotides 1 to 543 (FIGS. 3A–3D) was used as a probe. Equivalent poly(A) content of the samples was verified by analysis of replica dot hybridizations probed with $^{35}S$ labeled poly-dt (McClung et al, supra) (data not shown). Autoradiography was performed using Du Pont WDR film. Densitometry was performed using a RAS video image analysis system (Amersham/Loats).

Two prominent bands were observed in each of eight tissues examined; one of 1.9 kilobases and a second of 1.2 kilobases. The size of these two forms is consistent with the use of the two polyadenylation motifs seen in the Pro1 cDNA. If so, they would both encode the same protein. (The present inventors have isolated a clone that corresponds to the predicted 1.2 kilobase form and have verified this.) The total amount of prohibitin mRNA varies about four-fold among the tissues, and the distribution of prohibition mRNA between the 1.9 and 1.2 mRNAs varies by a similar amount from tissue to tissue.

EXAMPLE IX

Comparison to the Drosophila Cc Gene

The nucleotide sequence of Pro1 is approximately 67% identical throughout the predicted protein coding region to the Cc cDNA (Eveleth et al., *Nucl. Acids Res.* 14:6169–83 (1986)) of Drosophila (FIGS. 6A–6B), discounting a central 57 base region that is only found in the rat cDNA. The homology is much lower outside the protein coding region. Cc is a gene of unknown function that was discovered during a chromosome walk in the region of the dopa decarboxylase gene. Flies homozygous for non-functional alleles of Cc die during the larval to pupal metamorphosis (Eveleth et al., supra).

Three potential open reading frames (ORF) were found in sequencing the Cc cDNA (Eveleth et al., supra). The first one shares the same protein start as the rat ORF, is 27 amino acids long, and shares 22% identity to the rat ORF over this region (FIGS. 6A–6B). The second Cc ORF is 96 amino acids long and out of frame with the rat ORF. The third Cc ORF is 203 amino acids, and shares 55% homology with the rat ORF.

EXAMPLE X

Expression of Prohibitin

The plasmid containing the cDNA of prohibitin (PRO1) was digested with the restriction endonuclease, Eco R1. This digestion cuts out the complete cDNA in one piece. The cDNA was separated from the host vector by electrophoresis on a 1.5% agarose gel. The cDNA was retrieved from the agarose by electroelution. The cDNA was then purified by phenol:chloroform extraction and ethanol precipitation.

The expression vector was constructed using the plasmid pKK223-3 (Pharmacia-LKE). This plasmid was digested with the endonuclease, Eco R1 which causes a single cut 3' of a tac promoter and the ends were dephosphorylated with alkaline phosphatase to prevent ligation to itself. The plasmid and the cDNA of prohibitin were ligated by T4 ligase. The new construct was designated pKKPRO and was used to transform competent *E. coli* JM105 cells. The cells were grown on LB agar plates containing ampicillin. Single colonies were selected and were tested for the presence of the prohibitin cDNA in the sense direction.

Plasmid minipreps were prepared. The plasmids were digested with Xmn 1 which will cut the cDNA asymmetrically. Once the DNA was resolved on agarose gels, those containing prohibitin cDNA in the sense direction could be determined. Three clones were found to be in the sense direction and were designated pKKPRO-3, and -3.

It is important to realize that prohibitin is a growth inhibitor and that overproduction of the protein could be toxic to the cells. Therefore, the host plasmid, pKK233-3, was selected because the tac promoter which was 5' of the prohibitin cDNA is repressed by the lac repressor in the appropriate host bacteria (*E. coli* JM105). Under normal growth conditions for the bacteria, prohibitin will not be expressed. This allowed the isolation of the clone and the growth and maintenance of the bacterial stocks. However, the lac repressor can be suppressed by the addition of the IPTG (isopropyl-β-D-thiogalactoside to the medium. This allows the tac promoter to operate and prohibitin is then made.

Using the above system, the bacterial strain containing the recombinant plasmid, pKKPRO-5, was grown to late log phase then prohibitin expression was induced by addition of IPTG to the medium. After a period of induction, proteins were isolated and resolved by polyacrylamide gel electrophoresis in the presence of sodium dodecyl sulfate and β-mercaptoethanol. Using Western analysis, the prohibitin was detected only in the lanes that contained protein from bacteria containing sense prohibitin cDNA. This demonstrates that rat prohibitin was being expressed in the *E. coli* cells.

---

What is claimed is:

1. An isolated DNA molecule having the nucleotide sequence of Sequence I.D. No. 1.

2. An isolated DNA molecule wherein said DNA molecule has a nucleotide sequence that is an allelic or mammalian species variant of Sequence I.D. No. 1.

3. A construct comprising:
 (a) said DNA molecule according to claim 1; and
 (b) a vector for introducing said DNA molecule into a eucaryotic or procaryotic host cell.

4. The construct of claim 3 wherein said vector includes a regulatory sequence operatively linked to said DNA segment.

5. The construct of claim 3 wherein said vector is BLUESCRIPT.

6. The construct of claim 5 wherein said construct is Pro1.

7. The construct of claim 3 wherein said vector is pKK223-3.

8. The construct of claim 7 wherein said construct is pKKPRO.

9. A host cell stably transformed or transfected with the construct of claim 3 allowing expression of an antiproliferative protein encoded by said DNA molecule.

10. The host cell of claim 9 wherein said host cell is a eukaryotic or prokaryotic cell.

11. The host cell of claim 10 wherein said procaryotic cell is an *Escherichia coli* cell.

12. The host cell of claim 9 wherein said construct is pKKPRO.

13. An isolated DNA molecule encoding the amino acid sequence of Sequence I.D. No. 2.

14. An isolated DNA molecule wherein said molecule has a nucleotide sequence that encodes an allelic or mammalian species variant of the amino acid sequence of Sequence I.D. No. 2.

15. A construct comprising:
 (a) said DNA molecule according to claim 2; and
 (b) a vector for introducing said DNA molecule into a eucaryotic or procaryotic cell.

16. A host cell stably transformed or transfected with the construct of claim 15 allowing expression of an antiproliferative protein encoded by said DNA molecule.

17. A DNA probe consisting of an isolated DNA molecule having a nucleotide sequence that is a portion of the nucleotide sequence of Sequence I.D. No. 1 or of the complement of the nucleotide sequence of Sequence I.D. No. 1, which specifically hybridizes to prohibitin mRNA in 250 mM KCl, 2 mM Tris-HCl pH 7.9, at a temperature ranging from 37° C. to 60° C.

18. A DNA probe consisting of an isolated DNA molecule having a nucleotide sequence that is a portion of the nucleotide sequence of Sequence I.D. No. 1 or of the complement of the nucleotide sequence of Sequence I.D. No. 1, which specifically hybridizes to human chromosome 17q21–22 under a condition equivalent to 42° C. in a 50% formamide hybridization buffer.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 1696 base pairs
( B ) TYPE: nucleic acid
( C ) STRANDEDNESS: single -continued ( D ) TOPOLOGY: linear ( i i ) MOLECULE TYPE: DNA (genomic)

( x i ) SEQUENCE DESCRIPTION: SEQ ID NO:1:

```
CAGAAGGAGT  CATGGCTGCC  AAAGTGTTTG  AGTCCATCGG  AAAGTTCGGC  CTGGCCTTAG    60
CAGTTGCAGG  AGGCGTGGTG  AACTCTGCTC  TATATAACGT  GGATGCCGGA  CACAGAGCTG   120
TCATCTTCGA  CCGATTCCGT  GGCGTGCAGG  ACATCGTGGT  AGGGGAAGGG  ACTCACTTCC   180
TCATCCCCTG  GGTACAGAAG  CCAATCATCT  TTGACTGCCG  CTCTCGACCA  CGTAATGTGC   240
CGGTCATCAC  CGGCAGCAAA  GACTTGCAGA  ATGTCAACAT  CACACTACGT  ATCCTCTTCC   300
GGCCGGTGGC  CAGCCAGCTT  CCTCGTATCT  ACACCAGCAT  GGCGAGGAC   TATGATGAGC   360
GGGTGCTGCC  ATCTATCACC  ACAGAGATCC  TCAAGTCGGT  GGTGGCTCGA  TTCGATGCTG   420
GAGAATTGAT  TACCCAGCGA  GAGCTGGTCT  CCAGGCAGGT  GAGTGATGAC  CTCACAGAGC   480
GAGCAGCAAC  ATTCGGGCTC  ATCCTGGATG  ACGTGTCCCT  GACACATCTG  ACCTTCGGGA   540
AGGAGTTCAC  AGAGGCGGTG  GAAGCCAAAC  AGGTGGCTCA  GCAGGAAGCA  GAGAGAGCCA   600
GATTTGTGGT  GGAAAAGGCT  GAGCAGCAGA  AGAAGGCGGC  CATCATCTCT  GCTGAGGGTG   660
ACTCCAAAGC  GGCTGAGCTG  ATCGCCAACT  CACTGGCCAC  CGCCGGGGAT  GGCCTGATCG   720
AGCTGCGAAA  GCTGGAAGCT  GCTGAGGACA  TTGCTTATCA  GCTCTCCCGC  TCTCGGAACA   780
TCACCTACCT  GCCAGCAGGG  CAGTCCGTGC  TCCTCCAGCT  CCCCCAGTAA  GGCCAGCCAG   840
CCAGGGCCTC  CATCGCTCTG  AATGACGCCT  TCCTTCTGCC  CCACCCCAGA  ATCACTGTG    900
AAATTTAATG  ATTGGCTTAA  CATGAAGGAA  ATAAAGGTAA  AATCACTTCA  TATCTCTAAT   960
TATCAAATGA  AGCTTTTATT  GTTACACTTT  TTGCCCACTT  TCATAACAAA  ATTGCCAAGT  1020
GCCTATGCAG  ACTGGCCTTC  CACCCTGGGT  GCTGGCAGTC  GGCGGAAGAA  AGGCAGGGCA  1080
GTGTGTGTGG  TGGACGGGGA  GCCAGCTGGC  AGCCTGAGTA  GACCTTGAGC  CTCCATTCTG  1140
CCATATATTG  AAGATTTACA  GACAGTGGTG  CACACACGTG  AACCAAAAGC  AAGCCCTCAA  1200
TTTTTCCAGC  CATACGAACC  CGGACAGATG  CAGCTGAGGA  GGGCCTGAGG  AAGTGGTCTG  1260
TCTTAACTGT  AAGGCCATTC  CCTCTTAACC  GTGACCAGCG  GAAGCAGGTG  TGTGCGTGCG  1320
ACTAGGGCAT  GGAGTGAAGA  ATCTGCCCAT  CACGGTGGGT  GGGCCTAATT  TTGCTGCCCC  1380
CACCAGAGAC  CTAAACTTTG  GATAGACTTG  GATAGAATAA  GAGGCCTGGA  CTGAGATGTG  1440
AGTCCTGTGG  AAGACTTCCT  GTCCACCCCC  CACATTGGTC  CTCTCAAATA  CCAATGGGAT  1500
TCCAGCTTGA  AGGATTGCAT  CTGCCGGGGC  TGAGCACACC  TGCCAAGGAC  ACGTGCGCCT  1560
GCCTTCCCGC  TCCCTCTCTT  CGAGATTGCC  CTTCCTTCCC  AAGGGCTGTG  GGCCAGAGCT  1620
CCGAAGGAAG  CAATCAAGGA  AAGAAAACAC  AATGTAAGCT  GCTGTCAATA  AATGACACCC  1680
AGAGCCCCCC  TCAAAA                                                      1696
```

( 2 ) INFORMATION FOR SEQ ID NO:2:

( i ) SEQUENCE CHARACTERISTICS:
        ( A ) LENGTH: 272 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Ala  Ala  Lys  Val  Phe  Glu  Ser  Ile  Gly  Lys  Phe  Gly  Leu  Ala  Leu
 1              5                        10                       15
```

|     |     |     |     |     |     |     |     |     |     |     |     |     |     |     |
| --- | --- | --- | --- | --- | --- | --- | --- | --- | --- | --- | --- | --- | --- | --- |
| Ala | Val | Ala | Gly<br>20 | Gly | Val | Val | Asn | Ser<br>25 | Ala | Leu | Tyr | Asn | Val<br>30 | Asp | Ala |
| Gly | His | Arg<br>35 | Ala | Val | Ile | Phe | Asp<br>40 | Arg | Phe | Arg | Gly | Val<br>45 | Gln | Asp | Ile |
| Val | Val<br>50 | Gly | Glu | Gly | Thr | His<br>55 | Phe | Leu | Ile | Pro | Trp<br>60 | Val | Gln | Lys | Pro |
| Ile<br>65 | Ile | Pro | Asp | Cys | Arg<br>70 | Ser | Arg | Pro | Arg | Asn<br>75 | Val | Pro | Val | Ile | Thr<br>80 |
| Gly | Ser | Lys | Asp | Leu<br>85 | Gln | Asn | Val | Asn | Ile<br>90 | Thr | Leu | Arg | Ile | Leu<br>95 | Phe |
| Arg | Pro | Val | Ala<br>100 | Ser | Gln | Leu | Pro | Arg<br>105 | Ile | Tyr | Thr | Ser | Ile<br>110 | Gly | Glu |
| Asp | Tyr | Asp<br>115 | Gln | Arg | Val | Leu | Pro<br>120 | Ser | Ile | Thr | Thr | Glu<br>125 | Ile | Leu | Lys |
| Ser | Val<br>130 | Val | Ala | Arg | Phe<br>135 | Asp | Ala | Gly | Glu | Leu<br>140 | Ile | Thr | Gln | Arg | Glu |
| Leu<br>145 | Val | Ser | Arg | Gln | Val<br>150 | Ser | Asp | Asp | Leu | Thr<br>155 | Glu | Arg | Ala | Ala | Thr<br>160 |
| Phe | Gly | Leu | Ile | Leu<br>165 | Asp | Asp | Val | Ser | Leu<br>170 | Thr | His | Leu | Thr | Phe<br>175 | Gly |
| Lys | Glu | Phe | Thr<br>180 | Glu | Ala | Val | Glu | Ala<br>185 | Lys | Gln | Val | Ala | Asn<br>190 | Gln | Glu |
| Ala | Glu | Arg<br>195 | Ala | Arg | Phe | Val | Val<br>200 | Glu | Lys | Ala | Glu | Gln<br>205 | Gln | Lys | Lys |
| Ala | Ala<br>210 | Ile | Ile | Ser | Ala | Glu<br>215 | Gly | Asp | Ser | Lys | Ala<br>220 | Ala | Glu | Leu | Ile |
| Ala<br>225 | Asn | Ser | Leu | Ala | Thr<br>230 | Ala | Gly | Asp | Gly | Leu<br>235 | Ile | Glu | Leu | Arg | Lys<br>240 |
| Leu | Glu | Ala | Ala | Glu<br>245 | Asp | Ile | Ala | Tyr | Gln<br>250 | Leu | Ser | Arg | Ser | Arg<br>255 | Asn |
| Ile | Thr | Tyr | Leu<br>260 | Pro | Ala | Gly | Gln | Ser<br>265 | Val | Leu | Leu | Gln | Leu<br>270 | Pro | Gln |

( 2 ) INFORMATION FOR SEQ ID NO:3:

( i ) SEQUENCE CHARACTERISTICS:
( A ) LENGTH: 812 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| ATGGCTGCCA | AAGTGTTTGA | GTCCATCGGA | AAGTTCGGCC | TGGCCTTAGC | AGTTGCAGGA | 60 |
| GGCGTGGTGA | ACTCTGCTCT | ATATAACGTG | GATGCCGGAC | ACAGAGCTGT | CATCTTCGAC | 120 |
| CGATTCCGTG | GCGTGCAGGA | CATCGTGGTA | GGGGAAGGGA | CTCACTTCCT | CATCCCCTGG | 180 |
| GTACAGAAGC | CAATCATCTT | TGACTGCCGC | TCTCGACCAC | GTAATGTGCC | GGTCATCACC | 240 |
| GGCAGCAAAG | ACTTGCAGAA | TGTCAACATC | ACACTACGTA | TCCTCTTCCG | GCCGGTGGCC | 300 |
| AGCCAGCTTC | CTCGTATCTA | CACCAGCATT | GGCGAGGACT | ATGATGAGCG | GGTGCTGCCA | 360 |
| TCTATCACCA | CAGAGATCCT | CAAGTCGGTG | GTGGCTCGAT | TCGATGCTGG | AGAATTGATT | 420 |
| ACCCAGCGAG | AGCTGGTCTC | CAGGCAGGTG | AGTGATGACC | TCACAGAGCG | AGCAGCAACA | 480 |
| TTCGGGCTCA | TCCTGGATGA | CGTGTCCCTG | ACACATCTGA | CCTTCGGGAA | GGAGTTCACA | 540 |
| GAGGCGGTGG | AAGCCAAACA | GGTGGCTCAG | CAGGAAGCAG | AGAGAGCCAG | ATTTGTGGTG | 600 |

```
GAAAAGGCTG AGCAGCAGAA GAAGGCGGCC ATCATCTCTG CTGAGGGTGA CTCCAAAGCG      660

GCTGAGCTGA TCGCCAACTC ACTGGCCACC GCCGGGGATG GCCTGATCGA GCTGCGAAAG      720

CTGGAAGCTG CTGAGGACAT TGCTTATCAG CTCTCCCGCT CTCGGAACAT CACCTACCTG      780

CCAGCAGGGC AGTCCGTGCT CCTCCAGCTC CC                                    812
```

( 2 ) INFORMATION FOR SEQ ID NO:4:

( i ) SEQUENCE CHARACTERISTICS:
        ( A ) LENGTH: 753 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
ATGGCTGCTC AGTTCTTTAA TCGCATTGGC CAAATGGGCT CGGAGTGGCG TTTTGGGTGG       60

CGTTGTCAAT TCGGCATTAT ATAATGTGGA AGGCGGCCAC CGGGCGGTCA TCTTCGATCG      120

CTTCACCGGC ATCAAGGAGA ACGTGGTCGG CGAGGGTACC CACTTCTTCA TCCCATGGGT      180

GCAGCGGCCC ATCATCTTCG ACCATCCGG TCCCAGCCCC GCAACGTTCC AGAGATAACG       240

GGCAGCAAGG ATCTGCAGAA TGTCAACATC ACGCTCCGAA TCCTGTACCG CCCCATTCCA      300

GACCAGCTGC CAAGATCTA CACCATTCTC GGCCAGGACT ACGACGAGCG TGTCCTGCCC       360

TCCATCGCGC TGAGATGGT GTCGCAGCGC GTTTCCCAGG AACTGACTGT ACGTGCCAAG       420

CAGTTCGGCT TTATTCTGGA TGACATCTCG CTCACGCACT TGACCTTCGG TCGGGAGTTC      480

ACGCTGGCCG TCGAGATGAA GCAGGTGGCC CAGCAGGAGG CGGAGAAGGC GCGTTTTGTC      540

GTGGAGAAGG CCGAGCAACA GAAGCTGGCG TCCATTATTT CGGCGGAGGG TGATGCCGAA      600

CGCGCCTGTG TTGGCCAAGT CATTGCGAGG CCGGAGACGG TCTGGTGGAG CCTGCGACTG      660

ATTGACCGGC CGAGATATCG CCTCACCAGC TATCCCCGGT CCCGTGGAGT CGCCTACTTG      720

CCCAGCGGAC AGAGCCACGC TGCTCAATCT GCC                                   753
```

( 2 ) INFORMATION FOR SEQ ID NO:5:

( i ) SEQUENCE CHARACTERISTICS:
        ( A ) LENGTH: 276 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met Ala Ala Gln Phe Phe Asn Arg Ile Gly Gln Met Gly Leu Gly Val
 1               5                  10                  15

Ala Val Leu Gly Gly Val Val Asn Ser Ala Leu Tyr Asn Val Glu Gly
            20                  25                  30

Gly His Arg Ala Val Ile Phe Asp Arg Phe Thr Gly Ile Lys Glu Asn
        35                  40                  45

Val Val Gly Glu Gly Thr His Phe Phe Ile Pro Trp Val Gln Arg Pro
    50                  55                  60

Ile Ile Phe Asp Ile Arg Ser Gln Pro Arg Asn Val Pro Val Ile Thr
65                  70                  75                  80

Gly Ser Lys Asp Leu Gln Asn Val Asn Ile Thr Leu Arg Ile Phe Tyr
                85                  90                  95

Arg Pro Ile Pro Asp Gln Leu Pro Lys Ile Tyr Thr Ile Leu Gly Gln
```

|     |     |     |     |     |     | 100 |     |     |     |     | 105 |     |     |     |     | 110 |     |     |     |
| --- | --- | --- | --- | --- | --- | --- | --- | --- | --- | --- | --- | --- | --- | --- | --- | --- | --- | --- | --- |

Asp Tyr Asp Glu Arg Val Leu Pro Ser Ile Ala Pro Glu Val Leu Lys
     115                   120            125

Ala Val Val Ala Gln Phe Asp Ala Gly Glu Leu Ile Thr Gln Arg Glu
    130                135            140

Met Val Ser Gln Arg Val Ser Gln Glu Leu Thr Val Arg Ala Lys Gln
145                150                155              160

Phe Gly Phe Ile Leu Asp Asp Ile Ser Leu Thr His Leu Thr Phe Gly
            165            170              175

Arg Glu Phe Thr Leu Ala Val Glu Met Lys Gln Val Ala Gln Gln Glu
         180             185           190

Ala Glu Lys Ala Arg Phe Val Val Glu Lys Ala Glu Gln Gln Lys Leu
      195              200            205

Ala Ser Ile Ile Ser Ala Glu Gly Asp Ala Glu Ala Ala Gly Leu Leu
    210                215            220

Ala Lys Ser Leu Ala Glu Ala Gly Asp Gly Leu Val Glu Leu Arg Arg
225                230                235              240

Ile Glu Ala Ala Glu Asp Ile Ala Tyr Gln Leu Ser Arg Ser Arg Gly
            245            250              255

Val Ala Tyr Leu Pro Ser Gly Gln Ser Thr Leu Leu Asn Leu Pro Ser
         260             265           270

Thr Ile Ala Gln
    275

( 2 ) INFORMATION FOR SEQ ID NO:6:

( i ) SEQUENCE CHARACTERISTICS:
        ( A ) LENGTH: 1041 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
AACAAGATAA TGGCTGCTCA GTTCTTTAAT CGCATTGGCC AAATGGGCCT CGGAGTGGCC      60
GTTTTGGGTG GCGTTGTCAA TTCGGCATTA TATAATGTGG AAGGCGGCCA CCGGGCGGTC     120
ATCTTCGATC GCTTCACCGG CATCAAGGAG AACGTGGTCG GCGAGGGTAC CCACTTCTTC     180
ATCCCATGGG TGCAGCGGCC CATCATCTTC GACATCCGGT CCCAGCCCCG CAACGTTCCA     240
GTGATAACGG GCAGCAAGGA TCTGCAGAAT GTCAACATCA CGCTCCGAAT CCTGTACCGC     300
CCCATTCCAG ACCAGCTGCC CAAGATCTAC ACCATTCTCG GCCAGGACTA CGACGAGCGT     360
GTCCTGCCCT CCATCGCGCC TGAGGTGCTG AAGGCTGTGG TCGCCCAGTT CGACGCCGGC     420
GAGCTGATCA CCCAGCGTGA GATGGTGTCG CAGCGCGTTT CCCAGGAACT GACTGTACGT     480
GCCAAGCAGT TCGGCTTTAT TCTGGATGAC ATCTCGCTCA CGCACTTGAC CTTCGGTCGG     540
GAGTTCACGC TGGCCGTCGA GATGAAGCAG GTGGCCCAGC AGGAGGCGGA GAAGGCGCGT     600
TTTGTCGTGG AGAAGGCCGA GCAACAGAAG CTGGCGTCCA TTATTTCGGC GGAGGGTGAT     660
GCCGAAGCCG CTGGCCTGTT GGCCAAGTCA TTGGCCGAGG CCGGAGACGG TCTGGTGGAG     720
CTGCGACGTA TTGAGGCCGC CGAGGATATC GCCTACCAGC TATCCCGGTC CCGTGGTGTC     780
GCCTACTTGC CCAGCGGACA GAGCACGCTG CTCAATCTGC CATCGACCAT CGCGCAGTAG     840
CTGGGTGCAT CTAGTTCCGT TAAGTTGTAA CTACCTATAG CATTTACTAA GTACTTTTCG     900
ATTTTGTTTC TGCTGAAATA TGCACTACTC TAAAGCGTTC GCGCCCGACT GACTGGAGAA     960
```

TACTAAGCGA AACAACCAAA ATTTGTCTCA TGTAATCGGT TTTTCCATTA TCTTCCCGAT    1020

CGGGTTCGAA ATCCGGTCGC A    1041

( 2 ) INFORMATION FOR SEQ ID NO:7:

( i ) SEQUENCE CHARACTERISTICS:
        ( A ) LENGTH: 1345 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AACAAGCAAG ATAATGGCTG CTCAGTTCTT TAATCGCATT GGCCAAATGG GCTCGGAGTG    60

GCGTTTTGGG TGGCGTTGTC AATTCGGCAT TATATAATGT GGAAGGCGGC CACCGGGCGG    120

TCATCTTCGA TCGCTTCACC GGCATCAAGG AGAACGTGGT CGGCGAGGGT ACCCACTTCT    180

TCATCCCATG GGTGCAGCGG CCCATCATCT TCGGACCATC CGGTCCCAGC CCGCAACGT    240

TCCAGAGATA ACGGGCAGCA AGGATCTGCA GAATGTCAAC ATCACGCTCC GAATCCTGTA    300

CCGCCCCATT CCAGACCAGC TGCCCAAGAT CTACACCATT CTCGGCCAGG ACTACGACGA    360

GCGTGTCCTG CCCTCCATCG CGCCTGAGGT GCTGAAGGCT GTGGTCGCCC AGTTCGACGC    420

CGGCGAGCTG ATCACCCAGC GTGAGGTGAG TAAAAACATC AGGAGAGCCC TCAGTTTCTT    480

TAGGATAAAG CTTTTTTGAT GGGCCTTGTG TTTCACCAGA GGCGCTTATG TTTACTTAGT    540

ATCAGGTCAT CAGATCTCAT CGTATTTCAC GCGTATTTA TTTTCGATTT AAATTTGATT    600

GTGTAAGCAA GAACGCGATC TCGGCGCTTA AGTCTAGGCT TATTGCTCTT TTGAGAATTG    660

AAGCTTAAGA ATTGGATTAT TATTCAACTT ATGCAGTCGG AAATATAATA CTTTCATGCC    720

CGTACTTAAC GTGATTACCT CTTTGCAGAT GGTGTCGCAG CGCGTTTCCC AGGAACTGAC    780

TGTACGTGCC AAGCAGTTCG GCTTTATTCT GGATGACATC TCGCTCACGC ACTTGACCTT    840

CGGTCGGGAG TTCACGCTGG CCGTCGAGAT GAAGCAGGTG GCCCAGCAGG AGGCGGAGAA    900

GGCGCGTTTT GTCGTGGAGA AGGCCGAGCA ACAGAAGCTG GCGTCCATTA TTTCGGCGGA    960

GGGTGATGCC GAACGCGCCT GTGTTGGCCA AGTCATTGCG AGGCCGGAGA CGGTCTGGTG    1020

GAGCCTGCGA CTGATTGACC GGCCGAGATA TCGCCTCACC AGCTATCCCC GGTCCCGTGG    1080

AGTCGCCTAC TTGCCCAGCG GACAGAGCCA CGCTGCTCAA TCTGCCATCG ACCATCGCGC    1140

AGTAGCTGGG TGCATCTAGT TCCGTTAAGT TGTAACTACC TATAGCATTT CACTAAGTAC    1200

TTTTCGATTT TGTTTCTGCT GAAATATGCA CTACTCTAAA GCGTTCGGCC GACTGACTGG    1260

AGAATACTAA GCGAAACAAC CAAAATTTGT CTCATGTAAA TCGGTTTTTC CATTATCTTC    1320

CCGATCGGTT CGAAATCCGG TCGCA    1345

( 2 ) INFORMATION FOR SEQ ID NO:8:

( i ) SEQUENCE CHARACTERISTICS:
        ( A ) LENGTH: 279 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Met Ala Ala Gln Phe Phe Asn Arg Ile Gly Asn Met Gly Ser Glu Trp
1               5                   10                  15

Arg Phe Gly Trp Arg Cys Gln Phe Gly Ile Ile Met Trp Lys Ala Ala

|       |     |     |     |     |     |     | 20  |     |     |     | 25  |     |     |     | 30  |     |     |     |
|-------|-----|-----|-----|-----|-----|-----|-----|-----|-----|-----|-----|-----|-----|-----|-----|-----|-----|-----|

Thr Gly Arg Ser Ser Ser Ile Ala Ser Pro Ala Ser Arg Arg Thr Trp
        35                      40                  45
Ser Ala Arg Val Pro Thr Ser Ser Ser Met Gly Ala Ala Ala His His
    50                  55                  60
Leu Arg Thr Ile Arg Ser Gln Pro Arg Asn Val Pro Glu Ile Thr Gly
65                  70                  75                      80
Ser Lys Asp Leu Gln Asn Val Ala Ile Thr Leu Arg Ile Leu Tyr Arg
                85                  90                  95
Pro Ile Pro Asp Gln Leu Pro Lys Ile Tyr Thr Ile Leu Gly Gln Asp
            100                 105                 110
Tyr Asp Glu Arg Val Leu Pro Ser Ile Ala Pro Glu Xaa Xaa Xaa Xaa
        115                 120                 125
Xaa Xaa Xaa Xaa Xaa Xaa Xaa Xaa Xaa Xaa Xaa Xaa Xaa Xaa Xaa Met
        130                 135                 140
Val Ser Gln Arg Val Ser Gln Glu Leu Thr Val Arg Ala Lys Gln Phe
145                 150                 155                 160
Gly Phe Ile Leu Asp Asp Ile Ser Leu Thr His Leu Thr Phe Gly Arg
                165                 170                 175
Glu Phe Thr Leu Ala Val Glu Met Lys Gln Val Ala Gln Gln Glu Ala
            180                 185                 190
Glu Lys Ala Arg Phe Val Val Glu Lys Ala Glu Gln Gln Lys Leu Ala
        195                 200                 205
Ser Ile Ile Ser Ala Glu Gly Asp Ala Glu Arg Ala Cys Val Gly Gln
    210                 215                 220
Val Ile Ala Arg Pro Glu Thr Val Trp Trp Ser Leu Arg Leu Ile Asp
225                 230                 235                 240
Arg Pro Arg Tyr Arg Leu Thr Ser Tyr Pro Arg Ser Arg Gly Val Ala
                245                 250                 255
Tyr Leu Pro Ser Gly Gln Ser Ala Ala Ala Gln Ser Ala Ile Asp His
            260                 265                 270
Arg Ala Val Ala Gly Cys Ile
        275

( 2 ) INFORMATION FOR SEQ ID NO:9:

( i ) SEQUENCE CHARACTERISTICS:
  ( A ) LENGTH: 279 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:9:

```
TATGATGAGC GGGTGCTGCC ATCTATCACC ACAGAGATCC TCAAGTCGGT GGTGGCTCGA      60
TTCGATGCTG GAGAATTGAT TACCCAGCGA GAGCTGGTCT CCAGGCAGGT GAGTGATGAC     120
CTCACAGAGC GAGCAGCAAC ATTCGGGCTC ATCCTGGATG ACGTGTCCCT GACACATCTG     180
ACCTTCGGGA AGGAGTTCAC AGAGGCGGTG GAAGCCAAAC AGGTGGCTCA GCAGGAAGCA     240
GAGAGAGCCA GATTTGTGGT GGAAAAGGCT GAGCAGCAG                            279
```

( 2 ) INFORMATION FOR SEQ ID NO:10:

( i ) SEQUENCE CHARACTERISTICS:
  ( A ) LENGTH: 93 amino acids
  ( B ) TYPE: amino acid
  ( C ) STRANDEDNESS: single (  D  ) TOPOLOGY: linear (  i i  ) MOLECULE TYPE: peptide (  x i  ) SEQUENCE DESCRIPTION: SEQ ID NO:10:

| Tyr | Asp | Glu | Arg | Val | Leu | Pro | Ser | Ile | Thr | Thr | Glu | Ile | Leu | Lys | Ser |
|---|---|---|---|---|---|---|---|---|---|---|---|---|---|---|---|
| 1 | | | | 5 | | | | | 10 | | | | | 15 | |
| Val | Val | Ala | Arg | Phe | Asp | Ala | Gly | Glu | Leu | Ile | Thr | Gln | Arg | Glu | Leu |
| | | | 20 | | | | | 25 | | | | | 30 | | |
| Val | Ser | Arg | Glu | Val | Ser | Asp | Asp | Leu | Thr | Glu | Arg | Ala | Ala | Thr | Phe |
| | | 35 | | | | | 40 | | | | | 45 | | | |
| Gly | Leu | Ile | Leu | Asp | Asp | Val | Ser | Leu | Thr | His | Leu | Thr | Phe | Gly | Lys |
| | 50 | | | | | 55 | | | | | 60 | | | | |
| Glu | Phe | Thr | Glu | Ala | Val | Glu | Ala | Lys | Gln | Val | Ala | Gln | Gln | Glu | Ala |
| 65 | | | | | 70 | | | | | 75 | | | | | 80 |
| Glu | Arg | Ala | Arg | Phe | Val | Val | Glu | Lys | Ala | Glu | Gln | Gln | | | |
| | | | | 85 | | | | | 90 | | | | | | |

(  2  ) INFORMATION FOR SEQ ID NO:11:

(  i  ) SEQUENCE CHARACTERISTICS:
        (  A  ) LENGTH: 279 base pairs
        (  B  ) TYPE: nucleic acid
        (  C  ) STRANDEDNESS: single
        (  D  ) TOPOLOGY: linear (  i i  ) MOLECULE TYPE: DNA (genomic)

(  x i  ) SEQUENCE DESCRIPTION: SEQ ID NO:11:

```
TACGACGAGC   GTGTCCTGCC   CTCCATCGCG   CCTGAGGTGC   TGAAGGCTGT   GGTCGCCCAG         60
TTCGACGCCG   GCGAGCTGAT   CACCCAGCGT   GAGATGGTGT   CGCAGCGCGT   TTCCCAGGAA        120
CTGACTGTAC   GTGCCAAGCA   GTTCGGCTTT   ATTCTGGATG   ACATCTCGCT   CACGCACTTG        180
ACCTTCGGTC   GGGAGTTCAC   GCTGGCCGTC   GAGATGAAGC   AGGTGGCCCA   GCAGGAGGCG        240
GAGAAGGCGC   GTTTTGTCGT   GGAGAAGGCC   GAGCAACAG                                   279
```

(  2  ) INFORMATION FOR SEQ ID NO:12:

(  i  ) SEQUENCE CHARACTERISTICS:
        (  A  ) LENGTH: 93 amino acids
        (  B  ) TYPE: amino acid
        (  C  ) STRANDEDNESS: single
        (  D  ) TOPOLOGY: linear (  i i  ) MOLECULE TYPE: peptide (  x i  ) SEQUENCE DESCRIPTION: SEQ ID NO:12:

| Tyr | Asp | Glu | Arg | Val | Leu | Pro | Ser | Ile | Thr | Pro | Glu | Val | Leu | Lys | Ala |
|---|---|---|---|---|---|---|---|---|---|---|---|---|---|---|---|
| 1 | | | | 5 | | | | | 10 | | | | | 15 | |
| Val | Val | Ala | Glu | Phe | Asp | Ala | Gly | Glu | Leu | Ile | Thr | Gln | Arg | Glu | Met |
| | | | 20 | | | | | 25 | | | | | 30 | | |
| Val | Ser | Gln | Arg | Val | Ser | Gln | Glu | Leu | Thr | Val | Arg | Ala | Lys | Gln | Phe |
| | | 35 | | | | | 40 | | | | | 45 | | | |
| Gly | Phe | Ile | Leu | Asp | Asp | Ile | Ser | Leu | Thr | His | Leu | Thr | Phe | Gly | Arg |
| | 50 | | | | | 55 | | | | | 60 | | | | |
| Glu | Phe | Thr | Leu | Ala | Val | Glu | Met | Lys | Gln | Val | Ala | Gln | Gln | Glu | Ala |
| 65 | | | | | 70 | | | | | 75 | | | | | 80 |
| Glu | Lys | Ala | Arg | Phe | Val | Val | Glu | Lys | Ala | Glu | Gln | Gln | | | |
| | | | | 85 | | | | | 90 | | | | | | |

(  2  ) INFORMATION FOR SEQ ID NO:13:

( i ) SEQUENCE CHARACTERISTICS:
 ( A ) LENGTH: 279 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:13:

| | | | | | |
|---|---|---|---|---|---|
| TACGACGAGC | GGGTGTTACC | ATCTATCGGC | AATGAGGTTT | TAAAGTCTAT | AGTAGCTCAA | 60 |
| TTTGATGCTG | CTGAGTTAAT | TACACAGAGA | GAAATTATTT | CTCAAAAAAT | CAGAAAAGAG | 120 |
| CTTTCTACGA | GGGCCAACGA | ATTCGGTATT | AAGTTGGAAG | ATGTCTCTAT | CACTCATATG | 180 |
| ACGTTTGGTC | CCGAATTCAC | GAAAGCAGTT | GAGCAGAAGC | AGATTGCACA | GCAAGATGCC | 240 |
| GAAAGAGCCA | AATTCCTTGT | CGAAAAGGCG | GAGCAACAG | | | 279 |

( 2 ) INFORMATION FOR SEQ ID NO:14:

( i ) SEQUENCE CHARACTERISTICS:
 ( A ) LENGTH: 93 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:14:

```
Tyr Asp Glu Arg Val Leu Pro Ser Ile Gly Asn Glu Val Leu Lys Ser
 1               5                  10                  15

Ile Val Ala Gln Phe Asp Ala Ala Glu Leu Ile Thr Gln Arg Glu Ile
            20                  25                  30

Ile Ser Gln Lys Ile Arg Lys Glu Leu Ser Thr Arg Ala Asn Glu Phe
            35                  40                  45

Gly Ile Lys Leu Glu Asp Val Ser Ile Thr His Met Thr Phe Gly Pro
        50                  55                  60

Glu Phe Thr Lys Ala Val Glu Gln Lys Gln Ile Ala Gln Gln Asp Ala
 65                  70                  75                  80

Glu Arg Ala Lys Phe Leu Val Glu Lys Ala Glu Gln Gln
                    85                  90
```